(12) United States Patent
Schmuck et al.

(10) Patent No.: US 9,744,265 B2
(45) Date of Patent: Aug. 29, 2017

(54) 3-DIMENSIONAL CARDIAC FIBROBLAST DERIVED EXTRACELLULAR MATRIX

(71) Applicant: Wisconsin Alumni Research Foundation, Madison, WI (US)

(72) Inventors: Eric G. Schmuck, Deforest, WI (US); Kurt W. Saupe, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/330,486

(22) Filed: Jul. 14, 2014

(65) Prior Publication Data

US 2014/0328916 A1 Nov. 6, 2014

Related U.S. Application Data

(62) Division of application No. 13/593,969, filed on Aug. 24, 2012, now Pat. No. 8,802,144.

(60) Provisional application No. 61/575,658, filed on Aug. 25, 2011.

(51) Int. Cl.
| | |
|---|---|
| A61K 35/28 | (2015.01) |
| A61K 35/34 | (2015.01) |
| C12N 5/077 | (2010.01) |
| A61L 27/36 | (2006.01) |
| A61L 27/38 | (2006.01) |
| A61L 27/54 | (2006.01) |
| A61K 35/33 | (2015.01) |
| C12N 5/0775 | (2010.01) |
| A61K 38/00 | (2006.01) |

(52) U.S. Cl.
CPC .......... *A61L 27/3633* (2013.01); *A61K 35/28* (2013.01); *A61K 35/33* (2013.01); *A61K 35/34* (2013.01); *A61L 27/3687* (2013.01); *A61L 27/3834* (2013.01); *A61L 27/54* (2013.01); *C12N 5/0657* (2013.01); *C12N 5/0663* (2013.01); *A61K 38/00* (2013.01); *A61L 2300/414* (2013.01); *A61L 2430/20* (2013.01); *C12N 2513/00* (2013.01); *C12N 2533/90* (2013.01)

(58) Field of Classification Search
CPC .................................................. A61L 27/3633
See application file for complete search history.

(56) References Cited

U.S. PATENT DOCUMENTS

| | | | |
|---|---|---|---|
| 2006/0136027 | A1 | 6/2006 | Westlund et al. |
| 2006/0136028 | A1 | 6/2006 | Ross et al. |
| 2007/0014869 | A1 | 1/2007 | Matheny |

FOREIGN PATENT DOCUMENTS

| | | |
|---|---|---|
| WO | 2006095342 A2 | 9/2006 |
| WO | 2007025233 A1 | 3/2007 |
| WO | 2010039823 A2 | 4/2010 |

OTHER PUBLICATIONS

Poobalarahi et al. (Am J Physiol Heart Circ Physiol. 2006; H2924-H2932).*
Fanglian He (Jun. 5, 2011. Laemmli-SDS-PAGE. Bio-protocol Bio101: e80. http://www.bio-protocol.org/e80 ).*
Bradshaw et al. (J Invest Dermatol. 120: 949-955; 2003).*
Judah Folkman et al. (American Journal of Pathology. Feb. 1988; 130(2): 393-400).*
Bader, et al., Tissue Engineering of Heart Valves—Human Endothelial Cell Seeding of Detergent Acellularized Porcine Valves, European Journal of Cardio-thoracic Surgery, 1998, 14:279-284.
Baharvand, et al., The Effect of Extracellular Matrix on Embryonic Stem Cell-Derived Cardiomycocytes, Journal of Molecular and Cellular Cardiology, 2005, 38:495-503.
Cukierman, et al., Taking Cell-Matrix Adhesions to the Third Dimension, Science, 2001, 294:1708-1712.
Gnecchi, et al., Paracrine Mechanisms in Adult Stem Cell Signaling and Therapy, Circulation Research, 2008, 103:1204-1219.
Justice, et al., 3D Cell Culture Opens New Dimensions in Cell-Based Assays, Drug Discovery Today, 2009, 14(1/2):102-107.
Santiago, et al., Heterogeneous Differentiation of Human Mesenchymal Stem Cells in Response to Extended Culture in Extracellular Matrices, Tissue Engineering Part A, 2009, 15(12):3911-3922.
Silva, et al., Synthetic Extracellular Matrices for Tissue Engineering and Regeneration, Current Topics in Developmental Biology, 2004, 64:181-205.
Sreejit, et al., Cardiogel Supports Adhesion, Proliferation and Differentiation of Stem Cells with Increased Oxidative Stress Protection, European Cells and Materials, 2011, 21:107-121.
Vanwinkle, et al., Caridogel: A Biosynthetic Extracellular Matrix for Cardiomyocyte Culture, In Vitro Cell. Dev. Biol.—Animal, 1996, 32:478-485.
PCT International Search Report and Written Opinion, PCT/US2012/052252, Dec. 19, 2012.

* cited by examiner

*Primary Examiner* — Scott Long
(74) *Attorney, Agent, or Firm* — Quarles & Brady LLP

(57) ABSTRACT

A bioscaffold made from an isolated cardiac fibroblast-derived 3-dimensional extracellular matrix (ECM) is disclosed. The bioscaffold can be used as an epicardial patch for the delivery of therapeutic cells into myocardial tissue. Methods of making the 3-dimensional extracellular matrix using cultured cardiac fibroblasts are also disclosed.

8 Claims, 15 Drawing Sheets

A      B

3-DIMENSIONAL CARDIAC FIBROBLAST DERIVED EXTRACELLULAR MATRIX

CROSS-REFERENCE TO RELATED APPLICATIONS

This application is a divisional of U.S. patent application Ser. No. 13/593,969 filed Aug. 24, 2012, which claims the benefit of U.S. provisional Application No. 61/575,658 filed on Aug. 25, 2011. Each of these applications is incorporated by reference herein in its entirety.

STATEMENT REGARDING FEDERALLY SPONSORED RESEARCH/DEVELOPMENT

This invention was made with government support under HL092477 awarded by the National Institutes of Health. The government has certain rights in the invention.

BACKGROUND

The human heart continuously undergoes slow cellular turnover through apoptosis of cardiomyocytes and proliferation of cardiac progenitor cells at a rate of approximately 1% turnover a year (see Bergmann, O., et al., *Evidence for cardiomyocyte renewal in humans*. Science, 2009. 324 (5923): p. 98-102). This slow cardiomyocyte turnover is important for maintaining cardiac function from birth to old age; however, resident cardiac progenitor cells have shown little capacity for robust cardiac regeneration following myocardial injury such as that caused by a myocardial infarction (see Bolli, P. and H. W. Chaudhry, *Molecular physiology of cardiac regeneration*. Ann N Y Acad. Sci. 1211: p. 113-26). Thus, it is likely that any successful post-injury progenitor cell-based cardiac regeneration strategy would require administering progenitor cells such as stem cells from a source outside of the native injured cardiac tissue.

A major obstacle in developing cell-based regenerative strategies is the need to successfully transfer a sufficient number of therapeutic cells to the target location (Karp, J. M. and G. S. Leng Teo, *Mesenchymal stem cell homing: the devil is in the details*. Cell Stem Cell, 2009. 4(3): p. 206-16). For example, in the infarcted heart, transfer of therapeutic cells is challenged not only by the motion of the heart but also by its heightened electrical and structural instability (Fernandes, S., et al., *Autologous myoblast transplantation after myocardial infarction increases the inducibility of ventricular arrhythmias*. Cardiovasc Res, 2006. 69(2): p. 348-58). Despite these difficulties, some reports indicate that intramyocardial or intracoronary injection of potentially therapeutic cells following cardiac injury can result in modest improvement in cardiac function (see, e.g., Bolli, R., et al., *Cardiac stem cells in patients with ischaemic cardiomyopathy (SCIPIO): initial results of a randomised phase 1 trial*. Lancet, 2011. 378(9806): p. 1847-57; Price, M. J., et al., *Intravenous mesenchymal stem cell therapy early after reperfused acute myocardial infarction improves left ventricular function and alters electrophysiologic properties*. Int J Cardiol, 2006. 111(2): p. 231-9). However, to date, no study has reported the large scale engraftment of cells or functional cardiomyocyte regeneration in an infarcted heart.

An alternative to direct injection of potentially therapeutic cells is to place them in a biomatrix "patch" that can be affixed to a desired area of the heart, such as onto the epicardium. In this way, a patch pre-seeded with potentially therapeutic cells may release the cells, allowing them to migrate into the injured myocardium to facilitate regeneration directly, or may retain the cells in close proximity to the injury to facilitate regeneration indirectly (i.e., via paracrine factors) (see Gnecchi, M., et al., *Paracrine mechanisms in adult stem cell signaling and therapy*. Circ Res, 2008. 103(11): p. 1204-19). This approach has been attempted using patches made of synthetic materials (see Silva, E. A. and D. J. Mooney, *Synthetic extracellular matrices for tissue engineering and regeneration*. Curr Top Dev Biol, 2004. 64: p. 181-205), as well as naturally occurring biomaterials such as the extracellular matrix (ECM) remaining after decellularization of heart valves (Bader, A., et al., *Tissue engineering of heart valves—human endothelial cell seeding of detergent acellularized porcine valves*. Eur J Cardiothorac Surg, 1998. 14(3): p. 279-84), skeletal muscle (Borschel, G. H., R. G. Dennis, and W. M. Kuzon, Jr., *Contractile skeletal muscle tissue-engineered on an acellular scaffold*. Plast Reconstr Surg, 2004. 113(2): p. 595-602; discussion 603-4), or bovine dermis (Kouris, N. A., et al., *Directed Fusion of Mesenchymal Stem Cells with Cardiomyocytes via VSV-G Facilitates Stem Cell Programming*. Stem Cells Int, 2012. 2012: p. 414038). Notably, none of these patches are made from myocardial tissue, nor do any of them exhibit the unique structural characteristics of cardiac ECM.

The extracellular matrix (ECM) is the extracellular part of animal tissue that provides structural support to the cells, in addition to performing various other important functions. As such, it is the defining feature of connective tissue in animals. Fibroblasts play a central role in the synthesis and maintenance of the ECM. In vivo, the ECM has a 3-dimensional structure, which facilitates interaction on all sides of the cells that are associated with the ECM. Specifically, cells associated with the ECM may be in contact with ECM surfaces both above and below the cells. To accurately model ECM-cell interactions in vivo, any ECM structure that is used in vitro would likewise need to have a true 3-dimensional structure. A 3-dimensional ECM cannot be substantially flat, and would have a thickness of at least 20

The cardiac ECM is a unique 3-dimensional structure that facilitates the normal functioning of the heart. The arrangement of the cardiac ECM helps channel the contraction of each myocyte into one forceful contraction, ultimately ejecting blood from the ventricles into the circulation (see Akhyari, P., et al., *Myocardial tissue engineering: the extracellular matrix*. Eur J Cardiothorac Surg, 2008. 34(2): p. 229-41). Furthermore, the cardiac ECM has importance beyond providing structure to cardiac tissue. Specifically, it plays a role in cardiac wound healing (see Dobaczewski, M., et al., *Extracellular matrix remodeling in canine and mouse myocardial infarcts*. Cell Tissue Res, 2006. 324(3): p. 475-88; Jourdan-Lesaux, C., J. Zhang, and M. L. Lindsey, *Extracellular matrix roles during cardiac repair*. Life Sci. 87(13-14): p. 391-400), and may play a role in cardiac regeneration (see Akhyari, P., et al., *Myocardial tissue engineering: the extracellular matrix*. Eur J Cardiothorac Surg, 2008. 34(2): p. 229-41). Although the production of a thin (<0.1 µm), 2-dimensional putative cardiac ECM on the surface of culture plate has been previously reported (see VanWinkle, W. B., M. B. Snuggs, and L. M. Buja, *Cardiogel: a biosynthetic extracellular matrix for cardiomyocyte culture*. In Vitro Cell Dev Biol Anim, 1996. 32(8): p. 478-85), to our knowledge, there has been no previous report of the in vitro production of a 3-dimensional cardiac ECM.

It is increasingly recognized that ECM is highly tissue-specific, with the fibroblasts of a given tissue synthesizing an ECM having a unique combination of structural proteins and bioactive molecules (i.e. growth factors). Accordingly, transplantation of cells across different tissue types could be problematic (see Badylak, S. F., D. O. Freytes, and T. W. Gilbert, *Extracellular matrix as a biological scaffold material: Structure and function*. Acta Biomater, 2009. 5(1): p. 1-13).

In addition to not being of myocardial origin, biomaterials currently under investigation for use in cardiac cell transfer patches have other notable limitations. For example, a frequent issue with the use of synthetic or decellularized tissues in patches for therapeutic cell delivery to the myocardium is the inability of the patch to physically adhere to the epicardial surface. The patches often require the use of glue or sutures to hold the patch to the heart (see, e.g., Fiumana, E., et al., *Localization of mesenchymal stem cells grafted with a hyaluronan-based scaffold in the infarcted heart*. J Surg Res, 2012). If the patch does not maintain firm contact with the surface of the heart, the ability of the cells to transfer is decreased significantly. Furthermore, epicardial patches must not only adhere to the heart, but must also have the proper tensile strength and compliance to tolerate cardiac movement. If a patch's compliance does not match that of the ventricle and does not move with the beating heart, gaps may form under the surface, reducing cell transfer. Epicardial patches lacking tensile strength may disintegrate under the strains of a beating heart.

For these reasons, a patch made from a 3-dimensional bioscaffold that is cardiac-specific would be highly desirable to facilitate successful delivery of therapeutic cells to injured or diseased myocardial tissue.

BRIEF SUMMARY OF THE INVENTION

This application discloses an epicardial patch for facilitating the delivery of cells to myocardial tissue, as well the isolated cardiac extracellular matrix that makes up the patch and methods of making and using the same. Advantageously, the isolated cardiac extracellular matrix is truly 3-dimensional, is myocardial in origin and composition, adheres well to the wall of the heart without the need for glue or sutures, moves flexibly with the heart, and successfully facilitates the delivery of seeded cells into myocardial tissue.

In a first aspect, the disclosure encompasses a bioscaffold for facilitating the delivery of cells to myocardial tissue. The bioscaffold is made up of an isolated 3-dimensional cardiac extracellular matrix (ECM) derived from cardiac fibroblast cells in vitro. The isolated cardiac ECM has a composition similar to the in vivo 3-dimensional extracellular matrix that is unique to cardiac tissue. Along with other components, it is made up largely of the structural proteins fibronectin, collagen type I, collagen type III, and elastin, and the bioscaffold has a thickness of 20-500 µm. In some embodiments, the bioscaffold has a thickness range of 30-200 µm or of 50-150 µm. In some embodiments, fibronectin molecules make up from 60% to 90% of the structural protein molecules present in the ECM. In some embodiments, fibronectin molecules make up from 70% to 90% of the structural protein molecules present in the ECM. In some embodiments, fibronectin molecules make up from 80% to 90% of the structural protein molecules present in the ECM.

In some embodiments, the ECM further includes the structural protein collagen type V. Other structural proteins may also be included in the cardiac ECM. Preferably, the structural proteins of the cardiac ECM are not chemically cross-linked.

In addition to the structural proteins, the cardiac ECM may include matricellular proteins, such as growth factors and cytokines, as well as other substances. Non-limiting examples of other proteins that may be found in the cardiac ECM include latent transforming growth factor beta 1 (LTGFB-1), latent transforming growth factor beta 2 (LT-GFB-2), connective tissue growth factor (CTGF), secreted protein acidic and rich in cysteine (SPARC), versican core protein (VCAN), galectin 1, galectin 3, matrix gla protein (MGP), sulfated glycoprotein 1, protein-lysine 6-oxidase, and biglycan.

In certain preferred embodiments, the cardiac ECM is not attached to a solid surface, so that the bioscaffold can be readily used as an epicardial patch that can be applied to the heart wall. Optionally, the cardiac ECM is decellularized, and is thus essentially devoid of intact cardiac fibroblast cells. In some embodiments, the bioscaffold may be seeded with one or more cells that are therapeutic for cardiac disease or injury. Examples of therapeutic cells types that could be used to seed the bioscaffold include without limitation skeletal myoblasts, embryonic stem cells (ES), induced pluripotent stem cells (iPS), multipotent adult germline stem cells (maGCSs), bone marrow mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells (derived from iPS or ES cells), human mesenchymal stromal cells (derived from iPS or ES cells) skeletal myoblasts, or combinations thereof. Such embodiments also encompass methods for treating a subject having a cardiac disease or injury, wherein the surface of the subject's heart is contacted with a seeded epicardial patch as described above, and wherein the severity of the cardiac disease or injury is decreased. The method can be generally used in the treatment of any cardiac disease or injury wherein cardiomyocytes are lost, including without limitation in treating injury caused by an acute myocardial infarct, by a bacterial infection, by a viral infection, by congenital defect, or by heart failure.

In a second aspect, the disclosure encompasses a method for preparing a 3-dimensional cardiac extracellular matrix. The method includes the steps of (a) isolating cardiac fibroblasts from cardiac tissue; (b) expanding the cardiac fibroblasts in culture for 1-7 passages; and (c) plating the expanded cardiac fibroblasts into a culture having a cell density of 100,000 to 500,000 cells per $cm^2$. Optionally, step (c) involves plating the expanded cardiac fibroblasts into a culture having a cell density of 100,000 to 200,000 cells per $cm^2$. Under these conditions, the cardiac fibroblasts secrete a 3-dimensional cardiac extracellular matrix having a thickness of 20-500 µm that is attached to the surface on which the expanded cardiac fibroblasts are plated. Optionally, the cardiac ECM may have a thickness of 30-200 µm or 50-150 µm.

Optionally, the secreted cardiac ECM may be contacted with ethylenediaminetetraaceticacid (EDTA) to detach the cardiac ECM from the surface on which it is plated. The detached cardiac ECM forms a free floating bioscaffold that can be seeded with therapeutic cells and used as an epicardial patch, as described previously.

The cardiac ECM formed in the method can optionally be decellularized to remove any remaining cardiac fibroblasts from the ECM. Any decellularizing agent may be used to decellularize the cardiac ECM. Non-limiting examples of decellurizing agents known in the art include enzymatic agents, such as trypsin, endonucleases, or exonucleases; chemical agents, such as alkaline or acid solutions, hypertonic or hypertonic solutions, ethylenediaminetetraacetic acid (EDTA), ethylene glycol tetraacetic acid (EGTA), ammonium hydroxide, and peracetic acid; nonionic detergents, such as octylphenol ethylene oxide (Triton™-X 100); ionic detergents, such as sodium dodecyl sulfate (SDS) and polyether sulfonate (Triton™-X 200); and zwitterionic detergents, such as 3-[(3-cholamidopropyl)dimethylammonio]-1-propanesulfonate (CHAPS), sulfobetaine-10 and -16, and tri(n-butyl)phosphate.

In one embodiment, decellularization is performed by contacting the cardiac ECM with peracetic acid and subsequently rinsing the cardiac extracellular matrix with water. Alternatively, decellularization is performed by contacting the secreted cardiac extracellular matrix with ammonium hydroxide and octylphenol ethylene oxide (Triton™ X-100) and subsequently rinsing the cardiac extracellular matrix with water.

Optionally, the method further includes the step of seeding the cardiac extracellular matrix with one or more cells that are therapeutic for cardiac disease or injury. Examples of such therapeutic cells include without limitation skeletal myoblasts, embryonic stem cells (ES), induced pluripotent stem cells (iPS), multipotent adult germline stem cells (maGCSs), bone marrow mesenchymal stem cells (BM-SCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells (derived from iPS or ES cells), human mesenchymal stromal cells (derived from iPS or ES cells) skeletal myoblasts, or combinations thereof.

This aspect of the disclosure further encompasses a bioscaffold for facilitating cell delivery to myocardial tissue (i.e. an epicardial patch) that is made from the isolated 3-dimensional cardiac ECM produced by the method described above.

The disclosed compositions and methods are further detailed below.

BRIEF DESCRIPTION OF DRAWINGS

The invention will be better understood and features, aspects, and advantages other than those set forth above will become apparent when consideration is given to the following detailed description thereof. Such detailed description makes reference to the following drawings.

Figure 1:
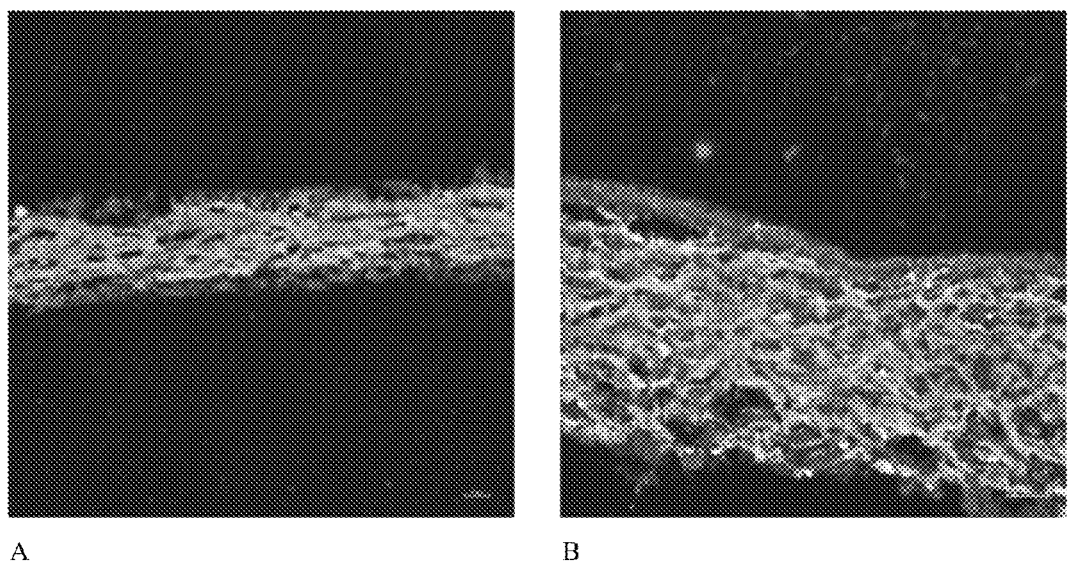
FIGS. 1A and B are photographs of representative paraffin embedded immunostained CF 3D-ECM decellularized with AH buffer. A and B) stained for fibronectin, collagen type 1, and DAPI. Individual colors not shown. Scale bar=10 μm.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

This application discloses an epicardial patch for facilitating the delivery of cells to myocardial tissue, as well as the isolated cardiac extracellular matrix that makes up the patch and methods of making and using the same. Advantageously, the isolated cardiac extracellular matrix is truly 3-dimensional, is myocardial in origin and composition, adheres well to the wall of the heart without the need for glue or sutures, moves flexibly with the heart, and successfully facilitates the delivery of seeded cells to myocardial tissue.

In a first aspect, the disclosure encompasses a bioscaffold for facilitating the delivery of cells to myocardial tissue. The bioscaffold is made up of an isolated 3-dimensional cardiac extracellular matrix (ECM) derived from cardiac fibroblast cells in vitro. By "isolated," we mean that the ECM is not in its conventional in vivo environment; rather, the ECM exists outside of the in vivo tissue with which is conventionally associated. Accordingly, isolated cardiac ECM is a bioengineered cardiac ECM that is not located within myocardial heart tissue, and the term does not encompass naturally occurring cardiac ECM.

By "3-dimensional," we mean that the ECM is not substantially flat (i.e., 2-dimensional), such that cells associated with the ECM may be in contact with ECM surfaces both above and below the cells. A 3-dimensional ECM has a thickness of at least 20 µm.

By "cardiac," we mean that the isolated ECM has a composition substantially similar to, but not necessarily identical to, the in vivo 3-dimensional extracellular matrix that is unique to cardiac tissue that is undergoing healing after myocardial disease or injury. Substantial similarity is based on the type and abundances of the structural proteins present in the ECM, as well as on the presence of characteristic matricellular proteins, such as growth factors and cytokines. In the healing cardiac ECM, more than 60% of the structural protein molecules present are fibronectin molecules.

The cardiac ECM includes the structural proteins fibronectin, collagen type I, collagen type III, and elastin, and may include other structural proteins as well. In some embodiments, the cardiac ECM includes the structural protein collagen type V.

Preferably, fibronectin molecules make up from 60% to 90% of the structural protein molecules present in the ECM. In some embodiments, fibronectin molecules make up from 70% to 90% of the structural protein molecules present in the ECM. In some embodiments, fibronectin molecules make up from 80% to 90% of the structural protein molecules present in the ECM.

The bioscaffold that is made from the ECM has a thickness of 20-500 µm. In some embodiments, the bioscaffold has a thickness range of 30-200 µm or of 50-150 µm. In some embodiments, more than 80% of the structural protein molecules present are fibronectin molecules.

Preferably, the structural proteins of the cardiac ECM are not chemically cross-linked.

In addition to the structural proteins, the cardiac ECM may include matricellular proteins, such as growth factors and cytokines, as well as other substance. Non-limiting examples of other proteins that may be found in the cardiac ECM include latent transforming growth factor beta 1 (LTGFB-1), latent transforming growth factor beta 2 (LTGFB-2), connective tissue growth factor (CTGF), secreted protein acidic and rich in cysteine (SPARC), versican core protein (VCAN), galectin 1, galectin 3, matrix gla protein (MGP), sulfated glycoprotein 1, protein-lysine 6-oxidase, and biglycan. In some embodiments, the ECM may optionally include one or more of transforming growth factor beta 1 (TGFB-1), transforming growth factor beta 3 (TGFB-3), epidermal growth factor-like protein 8, growth/differentiation factor 6, granulins, galectin 3 binding protein, nidogen 1, nidogen 2, decorin, prolargin, vascular endothelial growth factor D (VEGF-D), Von Willebrand factor A1, Von Willebrand factor A5 A, matrix metalprotease 14, matrix metalprotease 23, platelet factor 4, prothrombin, tumor necrosis factor ligand superfamily member 11, and glia derived nexin.

In certain preferred embodiments, the cardiac ECM is not attached to a solid surface, so that the bioscaffold can be readily used as an epicardial patch that can be applied to the surface of the heart wall. Optionally, the cardiac ECM is decellularized, and is thus essentially devoid of intact cardiac fibroblast cells. In some embodiments, the bioscaffold may be seeded using methods that are known in the art with one or more cells that are therapeutic for cardiac disease or injury. Examples of therapeutic cells types that could be used to seed the bioscaffold include without limitation skeletal myoblasts, embryonic stem cells (ES), induced pluripotent stem cells (iPS), multipotent adult germline stem cells (maGCSs), bone marrow mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells (derived from iPS or ES cells), human mesenchymal stromal cells (derived from iPS or ES cells) skeletal myoblasts, or combinations thereof. All of these cell types are well-known in the art.

Such embodiments also encompass methods for treating a subject having a cardiac disease or injury, wherein the surface of the subject's heart is contacted with a seeded epicardial patch as described above, and wherein the severity of the cardiac disease or injury is decreased. As demonstrated in Examples 3 and 4 below, after being placed onto the heart surface, the patch adheres to the heart surface without the use of glue, sutures, or other methods to facilitate attachment to the heart surface. Thus, although the patch may be glued, sutured, or otherwise attached to the surface of the heart, these steps are not necessary in performing the method. The method can be generally used in the treatment of cardiac disease or injury wherein cardiomyocytes are lost, including without limitation in treating injury caused by an acute myocardial infarct, by a bacterial infection, by a viral infection, by congenital defect, or by heart failure.

In a second aspect, the disclosure encompasses a method for preparing a 3-dimensional cardiac extracellular matrix. The method includes the steps of (a) isolating cardiac fibroblasts from cardiac tissue; (b) expanding the cardiac fibroblasts in culture for 1-7 passages; and (c) plating the expanded cardiac fibroblasts into a culture having a cell density of 100,000 to 500,000 cells per cm$^2$. If the cell density is less than 100,000 cells per cm$^2$, the culture will fail to produce a 3-dimensional ECM. Optionally, step (c) involves plating the expanded cardiac fibroblasts into a culture having a cell density of 100,000 to 200,000 cells per cm$^2$.

The cardiac fibroblasts may be isolated using methods known in the art. Under these conditions, the cardiac fibroblasts secrete a 3-dimensional cardiac extracellular matrix having a thickness of 20-500 µm that is attached to the surface on which the expanded cardiac fibroblasts are plated. Optionally, the cardiac ECM may have a thickness of 30-200 µm or 50-150 µm.

In one embodiment, the cardiac fibroblasts are cultured in high glucose DMEM+10% FBS and 1% penicillin/streptomycin at 37° in a 5% CO$_2$ 100% humidity atmosphere for 10-14 days. Optionally, after it is formed, the secreted cardiac ECM may be contacted with ethylenediaminetetraaceticacid (EDTA) to detach the cardiac ECM from the surface on which it is plated. The detached cardiac ECM forms a free floating bioscaffold that can seeded with therapeutic cells and used as an epicardial patch, as described previously.

The cardiac ECM formed in the method can optionally be decellularized to remove any remaining cardiac fibroblasts from the ECM. Any decellularizing agent may be used to decellularize the cardiac ECM. Non-limiting examples of decellurizing agents known in the art include enzymatic agents, such as trypsin, endonucleases, or exonucleases; chemical agents, such as alkaline or acid solutions, hypertonic or hypertonic solutions, ethylenediaminetetraacetic acid (EDTA), ethylene glycol tetraacetic acid (EGTA), ammonium hydroxide, and peracetic acid; nonionic detergents, such as octylphenol ethylene oxide (Triton™-X 100); ionic detergents, such as sodium dodecyl sulfate (SDS) and polyether sulfonate (Triton™-X 200); and zwitterionic detergents, such as 3-[(3-cholamidopropyl)dimethylammonio]-1-propanesulfonate (CHAPS), sulfobetaine-10 and -16, and tri(n-butyl)phosphate.

In one embodiment, decellularization is performed by contacting the cardiac ECM with peracetic acid (PAA) and subsequently rinsing the cardiac extracellular matrix with water. Alternatively, decellularization is performed by contacting the secreted cardiac extracellular matrix with ammonium hydroxide (AH) and octylphenol ethylene oxide (Triton™ X-100) and subsequently rinsing the cardiac extracellular matrix with water. Each method produces a different cardiac ECM that can further be distinguished from the cardiac ECM which is not decellularized, although all three cardiac ECMs contain a similar composition as defined by the structural proteins present.

Optionally, the method further includes the step of seeding the cardiac extracellular matrix with one or more cells that are therapeutic for cardiac disease or injury, using cell seeding methods that are well known in the art. Examples of such therapeutic cells include without limitation skeletal myoblasts, embryonic stem cells (ES), induced pluripotent stem cells (iPS), multipotent adult germline stem cells (maGCSs), bone marrow mesenchymal stem cells (BM-SCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), human mesenchymal stem cells (derived from iPS or ES cells), human mesenchymal stromal cells (derived from iPS or ES cells), or combinations thereof.

This aspect of the disclosure further encompasses a bioscaffold for facilitating cell delivery to myocardial tissue (i.e. an epicardial patch) that is made from the isolated 3-dimensional cardiac ECM produced by the method described above.

The following abbreviations and acronyms are used in this application: CF, cardiac fibroblast; CF-ECM, cardiac fibroblast-derived extracellular matrix; ECM, extracellular matrix; EDTA, ethylenediamine-N,N,N',N'-tetraacetic acid; DMAM, Dulbecco's modified eagle's medium; FBS, fetal bovine serum; FISH, fluorescence in situ hybridization; hMSC, human mesenchymal stromal cells; MI, myocardial infarction; PAA, Peracetic acid; PBST, phosphate buffer saline Tween®-20 (Polyethylene glycol sorbitan monolaurate).

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1: Production and Characterization of Cardiac Derived 3-Dimensional Extracellular Matrix In this Example, we generated a 3D-ECM using cardiac fibroblasts that is measured by confocal microscopy to be between 30-150+µm thick. Additionally, we devised multiple ways to remove the fibroblasts (decellularization), which allow for the study of the effect of cellular debris on stem cell attachment, proliferation and differentiation. Controlling (varying) the cell debris content is important because cellular debris is highly prevalent in the early phases of cardiac healing, and has largely been overlooked as a factor impacting therapeutic cell adhesion and differentiation. This new method of generating cardiac specific extracellular matrix will facilitate in vitro studies of stem cell interactions with a cardiac specific matrix.

An important first step in studying the CF 3D-ECM is carrying out detailed analyses of its composition and structure. This was done using bottom-up 2D-(strong cation exchange) mass spectrometry and confocal microscopy. Additionally, the effects of the matrix on cell morphology, proliferation and differentiation were studied using confocal microscopy, proliferation assay and quantitative PCR gene analysis.

Methods

Isolation of Cardiac Fibroblasts.

The technique for isolating cardiac fibroblasts is adapted from previously published reports (see Baharvand, H., et al., *The effect of extracellular matrix on embryonic stem cell-derived cardiomyocytes.* J Mol Cell Cardiol, 2005. 38(3): p. 495-503). Briefly, male Lewis rats (260-400 g) were sacrificed by $CO_2$ asphyxiation, hearts rapidly excised, atria removed and ventricles placed into ice cold PBS with 1% penicillin/streptomycin. Hearts were finely minced then placed into 10 ml digestion media (DMEM, 73 U/ml collagenase 2, 2 µg/ml pancreatin (4×)) and incubated at 37° C. with agitation for 35 minutes. The digest mixture was centrifuged at 1000×g for 20 minutes at 4° C. The resulting cell pellet was suspended in 10 mls of fresh digestion media and incubated at 37° C. with agitation for 30 minutes. The resulting digest was sieved through a 70 µm cell strainer and digest solution diluted with 10 ml of culture media (DMEM, 10% FBS, 1% penicillin/streptomycin). The cell suspension was then centrifuged at 1000×g for 20 minutes at 4° C. The cell pellet was suspended in 16 ml culture media and plated into two T75 culture flasks (8 ml per flask). The cells were allowed to attach under standard culture conditions (37° C., 5% $CO_2$, 100% humidity) for 2 hours, then non-adherent cells removed by washing with PBS and culture media replaced. Primary cardiac fibroblast cultures were typically confluent in 4-7 days.

Generation of 3-Dimensional Cardiac Fibroblast Extracellular Matrix.

Cardiac fibroblasts (Passage 1-7) were plated at a density of approximately $1.1 \times 10^5$ to $2.2 \times 10^5$ per $cm^2$ in high glucose DMEM+10% FBS and 1% penicillin/streptomycin and cultured at 37° C., 5% $CO_2$ and 100% humidity for an average of 10±3 days. Removal of the cardiac fibroblasts from the matrix was done by several different methods, as explained below.

Method 1: Matrix Coated Culture Surface (Ammonium Hydroxide/Triton X-100, "Clean Matrix").

Cardiac fibroblasts were removed from the secreted extracellular matrix by incubation with 20 mM ammonium hydroxide+0.1% Triton™ X-100 (AH buffer) for 24-48 hours at 4° C. with constant agitation. The resulting matrix was then rinsed repeatedly with sterile water followed by PBS or culture media. For this method, the cardiac fibroblasts were plated onto collagen type 1 coated dishes, which give the 3D-CF ECM a foundation to attach to so it will not lift off during decellularization.

Method 2: Matrix Coated Culture Surface (Peracetic Acid, "Dirty Matrix").

Cardiac fibroblasts were removed from the secreted extracellular matrix by incubation with 0.15% peracetic acid (PAA buffer) for 24-48 hours at 4° C. with constant agitation. The resulting matrix was then rinsed repeatedly with sterile water followed by PBS or culture media. PAA does not remove the matrix from the surface of the plate, so collagen type 1 was not required to anchor the matrix to the dish.

Method 3: Matrix "Patch."

Cardiac fibroblasts and secreted extracellular matrix were removed from the culture dish as a single patch by incubation with 2 mM EDTA solution at 37° C. The resulting patch was then decellularized with either Method 1 or 2 described above.

Isolation of Bone Marrow Mesenchymal Stem Cells.

The technique for isolating bone marrow mesenchymal stem cells was adapted from previously published reports (see Tropel, P., et al., *Isolation and characterisation of mesenchymal stem cells from adult mouse bone marrow.* Exp Cell Res, 2004. 295(2): p. 395-406). Briefly, male Lewis rats (260-400 g) were sacrificed by $CO_2$ asphyxiation. Femurs and tibias were bilaterally excised and soft tissue removed. The bones were placed in ice cold PBS with 1% penicillin/streptomycin. In a sterile culture hood, the ends of the bones were removed and an 18 gauge needle and syringe used to flush the shafts of the bones with culture media (DMEM, 10% FBS, 1% penicillin/streptomycin). The resulting bone marrow was further dispersed by passage through a 21 gauge needle. Cell suspension was then centrifuged at 1000×g for 10 minutes at 4° C. and plated into a 100 mm culture dish. The cells were allowed to attach under standard culture conditions (37° C., 5% $CO_2$, 100% humidity) for 24 hours, then non-adherent cells were removed by washing with PBS and the culture media was replaced.

Bottom Up Mass Spectrometry:

In-Solution Trypsin Digestion.

All solutions were prepared fresh just prior to use with HPLC grade water. CF 3D-ECM patch was prepared using Method 3, as described above, and cut in half. The halves were decellularized by either Method 1 or 2. The resulting decellularized patch was suspended in 15 µl 8M Urea and then 20 µl of 0.2% ProteaseMax™ added. The CF 3D-ECM was then dissolved into solution by vortexing and pipetting. 58.5 µl of 50 mM $NH_4HCO_3$ was added to a final volume of 93.5 µl. The sample was then reduced by adding 1 µl of 0.5 M DTT and incubating at 56° C. for 20 minutes. 2.7 µl of 0.55 M iodoacetamide was added and incubated for 15 minutes at room temperature in the dark. 1 µl of 1% ProteaseMax™ and 2 µl of 1 µg/µl Trypsin Gold™ added and incubated overnight at 37° C. The following day, 0.5 µl of trifluoroacetic acid was added to a final concentration of 0.5% to stop the reaction. The sample was then centrifuged at 14,000×g for 10 minutes at 4° C. and the cleared supernatant transferred to a fresh 1.5 ml protease-free tube.

2D Liquid Chromatography Mass Spectrometry.

2 µl of sample was injected onto an Eksigent 2D nanoLC chromatography system and eluted into a Thermo Finnigan LTQ Mass Spectrometer. The sample was retained on an Agilent Zorbax SB300-C8 trap and eluted by reverse phase gradient onto a 0.100 mm×100 mm emitter packed in-house with 5 µm bead 300 angstrom pore MagicC18 material. Mobile phase solution consisted of a water and 0.1% formic acid aqueous phase and a 0.1% formic acid in 50% acetonitrile:ethanol organic phase. The gradient ran from 1 to 60 minutes and from 5 to 35% organic with a 95% wash. Eluent was ionized by a positive 3000V nanoESI and analyzed by a Data Dependent triple play template. The top 5 m/z were selected by intensity, charge state was analyzed by zoom scan, and MS/MS were performed with wideband activation, dynamic exclusion of 1 for 60 seconds with a list of 300 m/z and a width of +/−1.5/0.5 m/z, collision energy of 35%, and noise level of 3000NL.

Sequest searches were performed via Bioworks 3.0 using a downloaded Swissprot database for Rat (October 2010) and its reversed sequences. Search parameters included trypsin digestion, 1 missed cleavage, amino acid length of 6 to 100 with tolerance of 1.4 da, dynamic modifications of methionine methylation (+14 da) and cysteine carboxyamidomethylation (+57 da). Results were filtered to less than 5% False Discovery Rate (FDR), defined by number of proteins identified with reversed sequences divided by the total number proteins identified minus reversed number, multiplied by 100.

Confocal Microscopy:

Paraffin Embedded CF 3D-ECM Patch Slides.

CF 3D-ECM patches were fixed in fresh 3.6% paraformaldehyde then embedded in paraffin and sectioned in 5 µm sections and mounted on slides. Slides were deparaffinized by two incubations in xylene for 5 minutes each followed by rehydration: 100% ethanol 2×5 minutes, 90% ethanol 2×5 minutes, 80% ethanol 1×5 minutes, 50% ethanol 1×5 minutes, water 2×5 minutes. A hydrophobic barrier was applied around the samples and the slides incubated with 0.1% trypsin solution for 10 minutes at 37° C. Slides were rinsed under running water and washed 2×5 minutes in PBS. A sodium citrate heat retrieval was performed by incubation in 10 mM Sodium citrate, 0.05% Tween®-20 buffer pH 6 for 60 minutes in an Oster® rice steamer (temperature approximately 95-100° C.). The staining dish was removed from the rice steamer and the slides were cooled for 20 minutes at room temperature then blocked with 1% bovine serum albumin in PBST for 1 hour at room temperature. Primary antibodies were added at a dilution of 1:50 (all antibodies except when noted were purchased from Santa Cruz Biomedical) and incubated at 37° C. for 1 hour. Slides were then washed 3×5 minutes in PBST and incubated in secondary antibodies at 1:1000 dilution in 1% bovine serum albumin in PBST (all secondary antibodies purchased from Invitrogen) for 1 hour at room temperature in the dark. Slides were then washed 2×5 minutes in PBST and counter stained with 1 µg/ml DAPI for 10 minutes followed by 1 wash in PBST and a final rinse in water. Cover slips were then mounted with aqueous mounting media and the edges sealed with quick dry, clear nail polish. Slides were imaged at the W. M Keck Laboratory for Biological Imaging with a Nikon MR scanning confocal microscope.

ECM Coated Coverslips.

Cardiac fibroblasts cultured on glass covers slips were decellularized using either Method 1 or 2 as discussed previously, then fixed with −20° C. methanol for 20 minutes. The cover slips were washed with 1% bovine serum albumin in PBST 3×5 minutes each, then blocked in 1% bovine serum albumin in PBST for 1 hour at room temperature. Primary antibodies were added at a concentration of 1:50 and incubated overnight at 4° C. with gentle agitation. Cover slips were then washed 3×5 minutes in 1% bovine serum albumin in PBST. Secondary antibodies were added at 1:1000 dilution and incubated for 1 hour at room temperature in the dark. Cover slips were then washed 2×5 minutes then counter stained with 1 µg/ml DAPI for 10 minutes at room temperature in the dark. Covers slips were then washed with 1% bovine serum albumin in PBST for 5 minutes and rinsed in water, then mounted to slides with aqueous mounting media and sealed with fast dry nail polish. Slides were imaged at the W. M Keck Laboratory for Biological Imaging with a Nikon MR scanning confocal microscope.

Proliferation Assay:

Bone marrow derived mesenchymal stem cells were isolated as described previously. After expansion of the cells in culture, they were washed in PBS then trypsinized with 0.5% trypsin, 2.5 mM EDTA solution until free floating. Cells were then centrifuged at 1000×g for 10 minutes at 4° C. The supernatant was removed and the cells suspended in DMEM+10% FBS and 1% penicillin/streptomycin and counted on a hemocytometer using trypan blue. The cells were then seeded onto either tissue culture treated plastic or decellularized matrix at a concentration of $1.0 \times 10^5$ cells per 40 mm dish. Cells were cultured for 5 days then trypsinized as described above and recounted on a hemocytometer. Statistical analysis was carried out using a One-way ANOVA followed by a Tukey's post hoc test. $p<0.05$ was considered statistically significant.

Quantitative Real-Time PCR Gene Analysis:

RNA Isolation and Purification.

RNA was isolated from cells using the Purelink RNA Isolation Kit® (Invitrogen) according to manufacturer's directions. Briefly, cells were trypsinized as described above then pelleted by centrifugation at 1000×g for 10 minutes at 4° C. Cells were washed in PBS, and pelleted as above, then moved to a fresh RNase-free 1.5 ml tube. Cells were suspended in 300 of lysis buffer then aspirated through a 27½ gauge needle 15 to 20 times. 300 µl of 70% ethanol was mixed with the sample by vortexing and pipetting before being transferred to a spin cartridge and centrifuged at 12,000×g for 15 seconds at room temperature. The flow-through was discarded and 700 µl of wash buffer 1 was placed onto the spin cartridge and centrifuged at 12,000×g for 15 seconds at room temperature. 40 units of RNase free DNase 1 (Qiagen) were placed on the spin cartridge and incubated for 15 minutes at room temperature. 500 µl of wash buffer 1 was added to the spin cartridge and centrifuged at 12,000×g for 15 seconds at room temperature. The spin cartridge was washed twice as described above with two volumes of 500 µl wash buffer 2. The spin cartridge was then dried by centrifugation at 12,000×g for 3 minutes at room temperature and the RNA eluted from the spin cartridge by incubating with 30 µl of RNase free water followed by centrifugation at 12,000×g for 1 minute at room temperature. RNA amount and 260/280 absorbance ratio were read on a NanoDrop® ND-1000 spectrophotometer.

cDNA Synthesis.

Synthesis of cDNA was carried out using the $RT^2$ First Strand Kit (Qiagen) according to manufacturer's directions. Briefly, 475 ng of RNA was mixed with 2 µl of Genomic DNA elimination buffer and volume adjusted to 10 µl with RNase-free water. The RNA was then incubated for 5 minutes at 42° C. then placed on ice. Reverse-transcription master mix was made by mixing: 4 µl 5× buffer BC3, 1 µl control P2, 2 µl RE3 reverse transcription mix, 3 µl RNase-free water (10 µl total) for each sample. 10 µl of the reverse-transcription mix was added to each sample and incubated at 42° C. for 15 minutes then the reaction was stopped by immediately incubating the sample at 95° C. for 5 minutes. 91 µl of RNase-free water was then added to each sample and the samples stored at −80° C. until analyzed. Before analysis on a Custom Rat $RT^2$ Profiler PCR Array, the quality of the sample was tested on a Quality Control (QC) plate testing for reverse transcription, positive PCR control, genomic DNA contamination, no reverse transcription and no template controls.

Custom Rat $RT^2$ Profiler PCR Array.

A commercially available Rat Mesenchymal Stem Cell Profiler PCR array was customized to include four markers of cardiac differentiation. The kit was used according to manufacturer's directions. Briefly, 1350 µl 2×$RT^2$ SYBR Green Mastermix, 102 µl cDNA synthesis reaction and 1248 µl RNase-free water were gently mixed together by pipetting. The Profiler plate was loaded by adding 25 µl of the above reaction mix to each well. The plate was centrifuged at 1000×g for 3 minutes and cycled with the following program: 1 cycle 10 minutes at 95° C., 40 cycles of 15 seconds at 95° C., 1 minute 60° C. (fluorescence data collection). Data were analyzed using software available from SABioscience and false discovery rate was determined with the QVALUE package for R statistical software.

Results

Identification of Cardiac Fibroblasts.

In culture, fibroblasts often differentiate into myofibroblasts, a highly proliferative regulator of extracellular matrix synthesis and maintenance. These myofibroblasts are primarily responsible for generating granulation tissue after cardiac injury. First, we confirmed the identity of the isolated cell population by staining for discoidin domain receptor 2 (DDR2), a cardiac fibroblasts specific marker. Second, to test if the cardiac fibroblasts had adopted a myofibroblast phenotype, we stained for α-actin, which is expressed in myofibroblasts but not fibroblasts. The immunostaining assay demonstrated the robust expression of DDR2 in the isolated cell population, indicating that the cell population was highly enriched for cardiac fibroblasts. 24 hours after plating, the immunostaining assay showed the co-expression of α-actin and DDR2. This is consistent with a myofibroblast phenotype, suggesting the cells had adopted a highly proliferative state that is known to synthesize large amount of extracellular matrix.

Generation of CF 3D-ECM.

Simple extracellular matrices preparations such as fibronectin, laminin and collagen are often referred to as 2-dimensional due to the thin coating (<1 micron) obtained on the culture surface. 3-dimensional cell culture has been shown to impart cellular morphologies and growth characteristics that are similar to those observed in vivo (see Justice, B. A., N. A. Badr, and R. A. Felder, *3D cell culture opens new dimensions in cell-based assays*. Drug Discov Today, 2009. 14(1-2): p. 102-7).

To investigate the use of 3-dimensional culture technologies in cardioregenerative medicine, we developed two methods to denude cardiac fibroblasts from high density cultures in vitro. This resulted in the production of two distinct types of CF 3D-ECM. FIGS. 1A and B, which show a stained paraffin embedded matrix in a 5 µm section that is approximately 45-50 µm thick, demonstrate representative examples of Method 1, decellularization by ammonium hydroxide/Triton X-100 (AH). Decellularization Method 2 employed peracetic acid (PAA) to denude cardiac fibroblasts from high density cultures in vitro.

Generation of CF 3D-ECM Patch.

Figure 2:
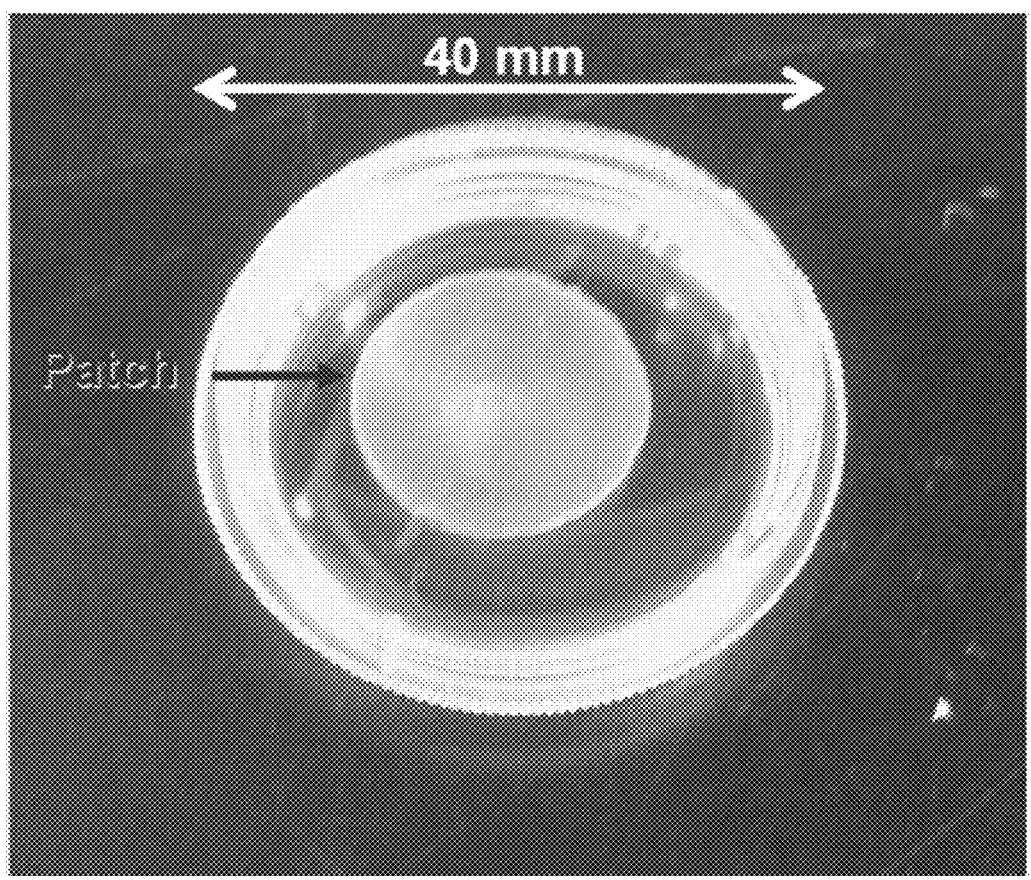
FIG. 2 is a photograph showing a cardiac fibroblast patch in a 40 mm diameter culture dish.

The use of tissue constructs for therapeutic cell transfer in cardioregenerative medicine is an area of intense research. The CF 3D-ECM that we have generated could be used for this purpose. We developed a method to remove the 3-dimensional fibroblast/matrix layer as a continuous sheet using EDTA. The sheet can then be decellularized using either AH or PAA. In addition to CF 3D-ECM patches, the non-decellularized cardiac fibroblast/matrix sheets can also be used as a viable patch option and are termed CF patches hereafter. FIG. 2 shows a representative CF patch. The patch produced in a 40 mm diameter culture dish contracts to approximately 20 mm in diameter after release from the plate.

Proteomics Based Analysis of CF 3D-ECM Structural and Matricellular Proteins:

Structural Protein Composition of CF 3D-ECM.

Fibroblasts synthesize a matrix unique to the tissue in which they reside. For this reason, we used 2D-mass spectrometry to evaluate the structural and matricellular proteins composing the matrix. Structural proteins were considered to be the extracellular proteins fibronectin, collagens, and elastin. We determined the breakdown of known structural and matricellular (non-structural proteins associated with the matrix) proteins as well as proteins that are neither structural nor matricellular (other) proteins found in AH and PAA decellularized matrix. Specifically, in the AH/Triton decellularized matrix, 31% of the proteins by total spectral counts were structural, 2% were matricellular, and 67% were neither (other). In the PAA decellularized matrix, 9% of the proteins by total spectral counts were structural, 1% were matricellular, and 90% were neither (other).

We further determined the distribution of structural proteins in the AH and PAA matrices. In the AH/Triton decellularized matrix, 89% of the structural protein by total spectral counts was fibronectin, 7.8% was collagen type 1, 2.0% was collagen type 3, and 0.9% was elastin. In the PAA decellularized matrix, 88.7% of the structural protein by total spectral counts was fibronectin, 8.3% was collagen type 1, 2.2% was collagen type 3, and 0.52% was elastin. While the two decellularization techniques created uniquely different matrices in terms of relative amounts of structural, matricellular, and non-structural/matricellular proteins, they did not significantly alter the relative amounts of structural proteins present in the matrix.

Analysis of Matricellular Proteins Contained in CF 3D-ECM.

The extracellular matrix is known to be a repository for bioactive molecules such as growth factor and cytokines. Such extracellular matrix associated bioactive molecules are termed matricellular proteins and are important for cell adhesion, proliferation, and differentiation. To identify the unique, low abundance bioactive molecules, Bottom-Up 2D-mass spectrometry was used. Table 1 details the growth factors and cytokines that were detected in the matrix. Thirty proteins were identified between the two decellularization conditions by bottom-up 2D mass spectrometry. Twenty-one matricellular proteins were identified in the PAA samples and twenty-three in AH matrix sample.

Figure 3:
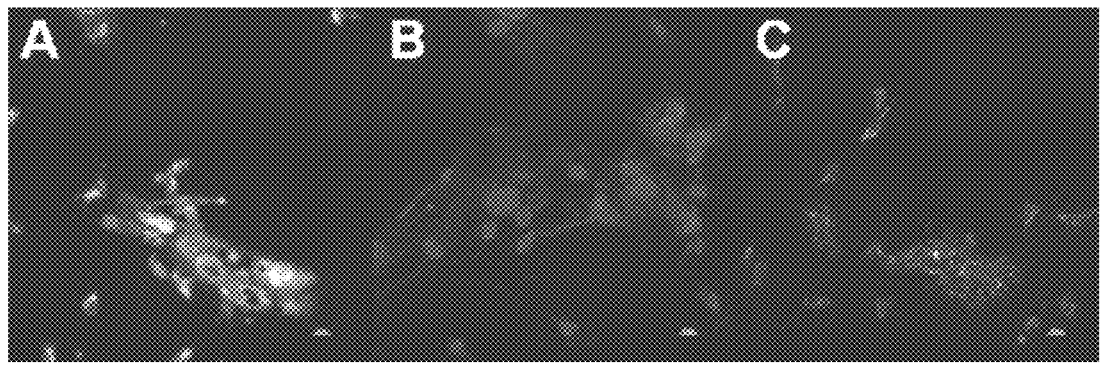
FIG. 3 are photographs showing BMSC surface marker expression. A) CD29 B) CD44 C) c-Kit.

To confirm the phenotype of the isolated BMSC, we stained for surface markers CD29, CD44, and c-kit (FIGS. 3A, B, and C respectively). As expected, the BMSC expressed all three markers.

BMSC Morphology in CF 3D-ECM.

Figure 4:
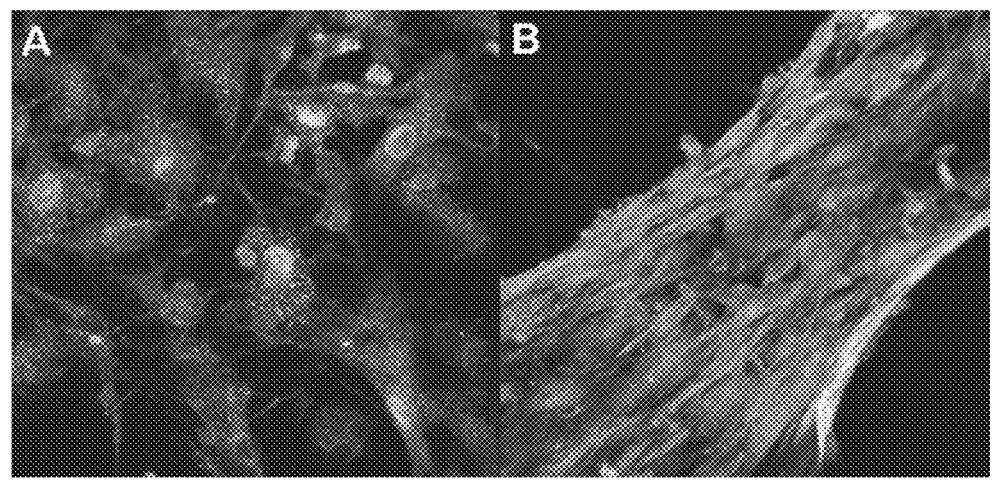
FIG. 4 are photographs showing BMSC morphology. A) BMSC grown on glass coverslips, stained for CD29, CD44, and c-kit (colors not shown). B) BMSC grown on CF 3D-ECM, stained for CD29, collagen type 1, CD44 (colors not shown). Scale bar=10 μm.

Cell morphology in 3-dimensional culture has been shown to be more in vivo like than 2-dimensional culture (see Justice, B. A., N. A. Badr, and R. A. Felder, *3D cell culture opens new dimensions in cell-based assays*. Drug Discov Today, 2009. 14(1-2): p. 102-7). To determine how culture of BMSC on CF 3D-ECM affects cell morphology, BMSC were plated onto either glass coverslips or coverslips coated with CF 3D-ECM. 48 hour after plating, cell morphology was examined with confocal microscopy. FIG. 4A demonstrates a typical in vitro fibroblastic BMSC morphology. FIG. 4B demonstrates that cells cultured on CF 3D-ECM take on an elongated morphology, aligning with the CF 3D-ECM.

Proliferation of BMSC on CF 3D-ECM.

Figure 5:
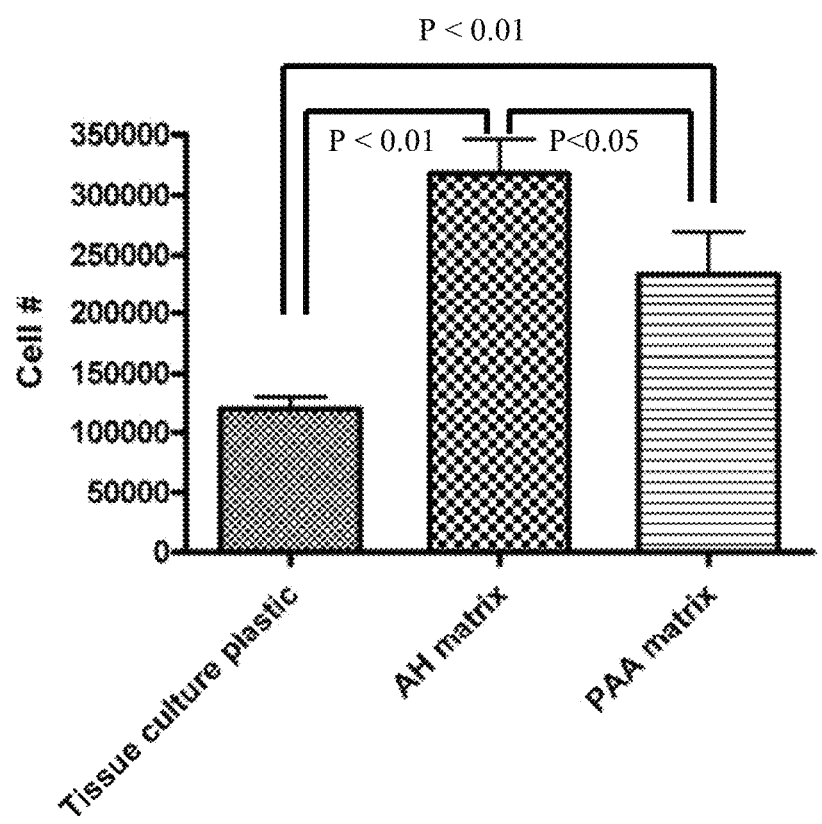
FIG. 5 is a bar graph showing that culturing BMSC on CF 3D-ECM increases proliferation of the cells, as compared to culturing the cells on tissue culture plastic. BMSC cultured on AH decellularized matrix had significantly increased proliferation compared to BMSC cultured on PAA decellularized matrix (n=5-6/group).

The surface on which a cell is cultured impacts the ability and/or rate at which the cell proliferates. With our detection of extensive matricellular proteins in the CF 3D-ECM it would seem reasonable that proliferation of BMSC would be affected. To determine the effect of CF 3D-ECM on proliferation, we performed a proliferation assay and found that culturing cells on CF 3D-ECM approximately doubled the proliferation rate of BMSC compared to those cultured on tissue culture treated plastic. Of the two matrix conditions, the "clean" AH matrix increased cell proliferation significantly more than PAA, 263% and 193% respectively compared to plastic (FIG. 5).

Figure 6:
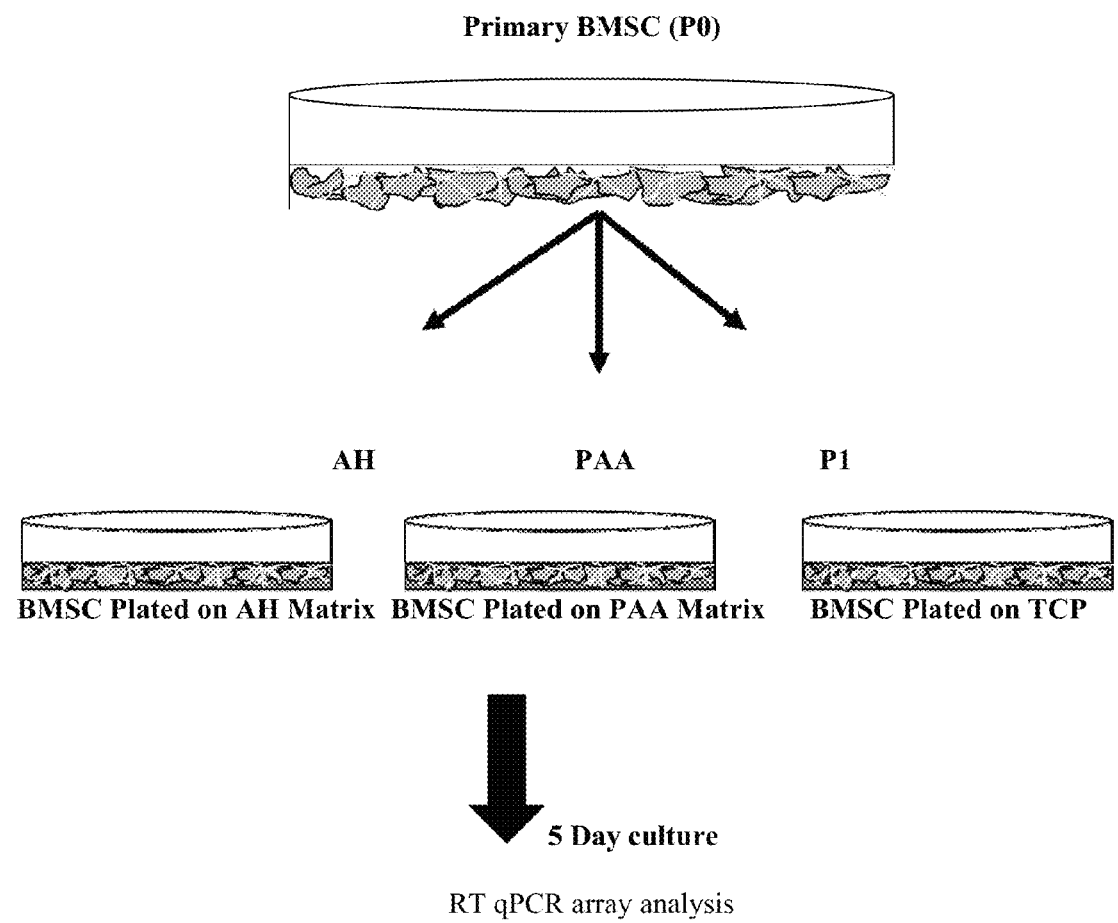
FIG. 6 is a schematic diagram showing the experimental design of gene analysis of BMSC cultured on AH, PAA, or P1 (cultured on tissue culture-treated plastic (TCP)).

It has been established that the surface/matrix a stem cell is cultured on impacts the differentiation state of the cell (see Santiago, J. A., R. Pogemiller, and B. M. Ogle, *Heterogeneous differentiation of human mesenchymal stem cells in response to extended culture in extracellular matrices*. Tissue Eng Part A, 2009. 15(12): p. 3911-22). To determine how the cardiac specific AH and PAA matrices effected gene expression of BMSC, including markers of stemness, mesenchymal specificity, and differentiation, we carried out an experiment according to FIG. 6. We passaged primary (P0) BMSC onto tissue culture plastic (P1), AH matrix, or PAA matrix (FIG. 6). Specifically, BM-derived MSCs were cultured for 5 days on plastic. The 'Passage 0' group was then removed and mRNA was collected. The 'Passage 1' group was passaged onto plastic, CF-derived matrix that was decellularized with ammonium hydroxide, or CF-derived matrix that was decellularized with PAA, and cultured for another 5 days before removal and collection of mRNA. As expected, passage alone had significant effects on BMSC gene expression. The expression of nineteen genes was altered by more than two-fold, with the expression of six genes increasing and thirteen genes decreasing (data not shown).

Interestingly, passage onto AH or PAA-treated matrix had significantly different effects in comparison to the cells cultured on tissue culture plastic (P1). Specifically, the AH matrix significantly altered the expression of twenty-three genes by greater than two-fold, with the expression of nine genes increasing and the expression of fourteen genes decreasing (data not shown). The PAA matrix significantly altered the expression of seven genes by greater than two-fold, with the expression of three genes increasing and the expression of four genes decreasing (data not shown). Twenty-four genes were significantly differentially expressed in BMSC cultured on PAA relative to AH matrix (data not shown). This finding is interesting, and may shed light on the effects of such factors as cell debris and matricellular proteins in cell attachment, proliferation, and gene expression.

Discussion

In this Example, we set out to 1) use novel culture techniques to induce cardiac fibroblasts to produce a 3D matrix that models phases of cardiac healing; 2) determine how different methods of fibroblast removal affect the protein composition of the 3D-ECM; and 3) determine how BMSC are affected by culture on 3D ECM of different protein compositions.

Using Novel Culture Techniques to Induce Cardiac Fibroblasts to Produce a 3-Dimensional Matrix that Models Phases of Cardiac Healing.

In vivo, cells residing within any organ exist in a 3-dimensional environment. Work by Cukierman et al. and others have demonstrated the profound effects that culturing cells in a 3-dimensional matrix can have on important cellular characteristics such as adhesion, proliferation, and migration (Cukierman, E., et al., *Taking cell-matrix adhesions to the third dimension*. Science, 2001. 294(5547): p. 1708-12).

Early attempts by VanWinkle to create a cardiac specific extracellular matrix resulted in deposition of extracellular matrix proteins onto the culture surface (VanWinkle, W. B., M. B. Snuggs, and L. M. Buja, *Cardiogel: a biosynthetic extracellular matrix for cardiomyocyte culture*. In Vitro Cell Dev Biol Anim, 1996. 32(8): p. 478-85). The matrix deposited using the VanWinkle technique was extremely thin, on the order of <0.1 µm in total thickness. A matrix of this thickness should not be considered 3-dimensional because it does not create an environment where cells can interact on all sides. In contrast, we were able to create cardiac specific matrix that is consistently >50 µm in thickness, with some preparations growing as large as 150+µm.

TABLE 1

Matricellular proteins found in CF 3D-ECM*

|  | Spectral Hits | |
| --- | --- | --- |
|  | PAA | AH |
| Proliferation/Differentiation | | |
| Transforming growth factor beta 1 | 0 | 1 |
| Transforming growth factor beta 3 | 1 | 4 |
| Latent transforming growth factor beta 1 | 2 | 2 |
| Latent transforming growth factor beta 2 | 2 | 10 |
| Connective tissue growth factor | 4 | 18 |
| Epidermal growth factor-like protein 8 | 0 | 1 |
| Growth/differentiatoin factor 6 | 0 | 1 |

TABLE 1-continued

Matricellular proteins found in CF 3D-ECM*

|  | Spectral Hits | |
| --- | --- | --- |
|  | PAA | AH |
| Granulins | 5 | 0 |
| SPARC | 14 | 13 |
| Versican Core Protein | 13 | 63 |
| Adhesion | | |
| Galectin 1 | 11 | 2 |
| Galectin 3 | 21 | 23 |
| Galectin 3 binding protein | 3 | 0 |
| Nidogen 1 | 19 | 0 |
| Nidogen 2 | 0 | 1 |
| Decorin | 0 | 1 |
| Prolargin | 1 | 9 |
| Angiogenesis | | |
| Vascular endothelial growth factor D | 1 | 0 |
| VonWillebrand factor A1 | 0 | 2 |
| VonWillebrand factor A5 A | 9 | 0 |
| Proteases | | |
| Matrix Metaloprotease 14 | 1 | 0 |
| Matrix Metaloprotease 23 | 0 | 1 |
| Other Matricellular Proteins | | |
| Matrix Gla Protein | 6 | 13 |
| Sulfated glycoprotein 1 | 46 | 2 |
| Platelet factor 4 | 0 | 1 |
| Protein-lysine 6-oxidase | 2 | 4 |
| Prothrombin | 1 | 2 |
| Tumor necrosis factor ligand superfamily member 11 | 0 | 1 |
| Biglycan | 15 | 15 |
| Glia derived nexin | 1 | 0 |

*Relative abundance of the proteins may be indicated by the number of spectral hits. Reliable quantification of the matricellular proteins based in this data is difficult, due to their low abundance.

We discovered that when cardiac fibroblasts were isolated and cultured they responded with an "injury" pattern of extracellular matrix production, synthesizing a matrix high in fibronectin, with lesser components including collagen types 1 and 3. This phenomenon allowed us to model some of the phases of cardiac healing. The composition of the structural proteins in CF 3D-ECM (Table 1) is similar to that of a second order matrix formed during cardiac healing process. Studies in the infarcted canine myocardium found that the second order matrix is primarily composed of fibronectin (64%) with small amounts of collagen types 1 and 3 (Dobaczewski, M., et al., *Extracellular matrix remodeling in canine and mouse myocardial infarcts*. Cell Tissue Res, 2006. 324(3): p. 475-88). In that study, fibronectin content peaked between 7-14 days post myocardial infarction.

While our data from isolated rat cardiac fibroblasts yielded a matrix with somewhat more fibronectin (89%) than in the canine, the overall composition of the CF 3D-ECM was more similar to second order matrix, formed during phase three of cardiac healing, than either normal cardiac extracellular matrix or a mature scar. Because of these structural similarities, we believe that we have created a matrix that models the 7-14 day period post myocardial infarction. This time frame may be ideal for therapeutic cell therapy, because of reduced inflammatory response. Furthermore, due to its high fibronectin content, such a matrix may be more conducive to cell adhesion than a mature scar with fully cross linked collagen as the primary component. Thus, our CF 3D-ECM holds promise as a reagent for the study of stem cell-ECM interaction within the healing myocardial extracellular matrix.

Determining how Different Methods of Fibroblast Removal Affect the Protein Composition of the 3D-ECM.

Cell debris is a natural component of the healing myocardium, especially in phases 1 (cardiomyocyte cell death) and 2 (acute inflammation). To date, the effects of cell debris on therapeutic cell adhesion, proliferation, and differentiation has gone relatively unstudied. We discovered that while the method of decellularization (AH or PAA) did not affect the composition of structural proteins (fibronectins, collagens, and elastin) in the matrix, it did effect the overall protein composition. PAA contained considerably more non-structural proteins compared to AH matrix, demonstrating that PAA creates a matrix with significantly more cell debris than decellularization with AH.

It is important to note that other proteins that are not structural or matricellular compose a large proportion of CF 3D-ECM. This may be to some degree an artifact of the method used to characterize and quantify relative proportions of extracellular matrix (structural) proteins. For example, to perform bottom up 2D-mass spectrometry one must first perform an in-solution trypsin digestion to produce peptides which can be sequenced by the instrument. This proved to be difficult on extracellular matrix proteins, due to their low solubility in solution, structural complexity, and resistance to degradation by trypsin. It is possible that non-structural matrix proteins were preferentially digested. Additionally, bottom up 2D-mass spectrometry is highly sensitive; we may be making a proverbial "mountain out of a mole hill", with the ability to detect even the most minor of proteins present in the matrix. Regardless of whether the high proportion of non-structural/matricellular proteins in CF 3D-ECM is a methodological artifact, the PAA decellularized CF 3D-ECM contained significantly more non-structural/matricellular proteins than the AH decellularized CF 3D-ECM, thus we consider the PAA matrix to be relatively "dirty" and the AH matrix to be relatively "clean".

We demonstrated that PAA and AH create two distinctively different matrices in regards to the amount of cell debris contained in/on the CF 3D-ECM, while maintaining the same extracellular matrix protein structural composition. The two distinctly different matrices resemble more specific phases of cardiac healing. PAA, with its greater proportion of cell debris, is more similar to phases 1 (cardiomyocyte cell death) and 2 (acute inflammation) of cardiac healing, while AH, with its relatively cleaner matrix, may more closely resemble phase 3 (granulation tissue formation).

Determining how BMSC are Affected by Culture on 3D ECM of Different Protein Compositions.

It has been well established that extracellular matrix has profound effects on cell morphology, proliferation, and differentiation (Cukierman, E., et al., *Taking cell-matrix adhesions to the third dimension*. Science, 2001. 294(5547): p. 1708-12). In our CF 3D-ECM, a likely cause of these matrix effects on cells is the presence of thirty specific matricellular proteins we identified by bottom up 2D mass spectrometry (Table 1). Ten of the thirty matricellular proteins identified are involved in cellular proliferation and differentiation. Several members of the transforming growth factor beta (TGF-β) super family were present in either active or latent form. TGF-β is known to be secreted by myofibroblasts and promotes cell proliferation. Consistent with this, we found that BMSC grown on CF 3D-ECM had markedly greater cellular proliferation (AH 263%, PAA 193%) compared to cells cultured on tissue culture treated plastic. Interestingly, proliferation was significantly greater on "clean" AH matrix compared to the "dirty" PAA matrix (p<0.05). This could be the result of cell debris limiting cell-extracellular matrix interactions. The higher level of cell debris in the PAA model may limit the cells access to the matricellular proteins, such as TGF-β, that promote proliferation.

Stem cells differentiate in response to passage in culture and to exposure to extracellular matrix. RT qPCR analysis of BMSC cultured on tissue culture plastic or CF 3D-ECM confirmed that both passage and CF 3D-ECM affected the cells' differentiation state as indicated by changes in gene expression. We did not observe a clear up or down regulation of a single differentiation pathway, likely due in large part to using an unselected heterogeneous BMSC cell population. Several firm conclusions can be made. First, AH and PAA decellularized matrices are very different. This is evident by the fact that of the 28 genes that had a greater than 2-fold difference in expression from P1 (passaged onto plastic), not a single gene was changed equally by both AH and PAA. Additionally, AH matrix may prevent some passage-induced differentiation. AH matrix completely reversed the passage effect of 5 genes (Adipoq, GDF5, BMP6, GDF7 and Tbx5). Finally, AH and PAA matrices do not promote cardiomyogenic differentiation. Only one cardiac gene was altered by any condition; troponin T expression was decreased 2-fold by AH matrix.

This work represents initial studies of the effect of CF 3D-EMC on a potentially therapeutic cell population (BMSC). We determined how MSC are affected by culture on 3D ECM of different protein compositions by evaluating proliferation and gene expression associated with mesenchymal stem cells. While CF 3D-ECM clearly accelerated the proliferation rate, analysis of gene expression associated with mesenchymal stem cells was more complex. It is clear that CF 3D-ECM did not cause an adoption of a cardiac phenotype. While the meaning of the gene changes is difficult to interpret, it is clear that even a relatively short culture time on CF 3D-ECM can induce BMSC to change phenotypes.

Summary.

We successfully generated a novel cardiac fibroblast derived 3-dimensional matrix (CF 3D-ECM) that has characteristics similar to the matrix synthesized during cardiac healing. Using two specific methods to decellularize the matrices, we were able to generate matrix with varying amounts of cell debris. The two distinctly different matrices induced large changes in proliferation rate and BMSC gene expression. This novel CF 3D-ECM holds promise as both a reagent for use in studying cell-matrix interactions (see Example 2) and as a bioscaffold "patch" for therapeutic cell transfer to the heart (see Examples 3 and 4).

Example 2: Dynamic Adhesion of Mesenchymal Stem Cells to Cardiac Fibroblast 3-Dimensional Extracellular Matrix Therapeutic cell adhesion and engraftment are essential to the success of cell-based therapy. Current techniques involving circulatory infusion (systemic or intracoronary) have been used in large scale clinical trials with mixed results, with extremely low reported retention rates for both systemic and intracoronary infusion. Intramyocardial injection (either epicardial or endocardial) tends to have greater cell retention rates than circulatory delivery modes and has the ability to deliver cells with limited extravasation potential, such as skeletal myoblasts. To date, studies quantifying cell retention in vivo have been difficult and expensive to perform.

To address this issue, we utilized an oscillatory dynamic adhesion assay developed by others to test the adhesion of BMSC to our CF 3D-ECM generated with AH or PAA and to cardiac fibroblasts (non-decellularized). We also developed a double ended antibody to CD44 and fibronectin in an attempt to increase adhesion of BMSC to CF 3D-ECM. We demonstrated that adhesion to CF 3D-ECM was impacted by the method of decellularization. Specifically, it appears that the increased presence of cell debris in the "dirty" PAA CF 3D-ECM significantly reduced BMSC adhesion to that matrix. Additionally, the presence of cardiac fibroblasts significantly reduced the ability of the BMSC to adhere to the underlying matrix. Finally, we failed to alter cell adhesion using a targeted antibody tethering approach.

We combined the microfluidics oscillatory adhesion assay developed in another lab with our CF 3D-ECM by culturing cardiac fibroblasts within the microchannels of a microfluidic device. Advantages of using this assay system include: 1) adhesion to a cardiac specific extracellular matrix can be measured quickly and is reproducible; 2) the oscillatory motion of the dynamic adhesion assay is similar to the pulsatile nature of cardiac tissue; 3) a limited number of cells are needed to carry out quantitative studies (in traditional continuous flow adhesion assays, large numbers of cell are needed to maintain a continuous flow); 4) The CF 3D-ECM can be manipulated to mimic the temporal aspect of cardiac healing using multiple decellularization techniques; and 5) treatments targeted at increasing therapeutic cell adhesion can be carried out, such as the antibody tethering experiments presented in this Example. We tested three preparations of CF 3D-ECM in an attempt to mimic different phases of cardiac healing.

Phase 1 and 2 (Cardiomyocyte Death and Acute Inflammation).

One feature of early cardiac healing is the presence of large amount of cellular debris infesting the injured area. The presence of zones of dense cell debris are termed contraction bands. To date, cell debris has largely gone unstudied as a factor affecting therapeutic cell adhesion. Given the importance of cell-extracellular matrix interaction during adhesion, any inhibition of receptor binding interactions could have large effects on the ability of a potentially therapeutic cell to bind to the matrix.

Phase 3 and 4 (Granulation Tissue Formation and Scar Remodeling/Repair).

Granulation tissue formation is initiated once macrophages remove a majority of the dead cells and debris from the injured area. Matrix deposition during healing is an orderly process. A first order matrix is composed of primarily fibrin from the blood. This is replaced by a second order matrix secreted by myofibroblasts infiltrating the damaged tissue. This second order matrix is composed primarily of fibronectin with smaller amounts of collagen types I and III. The second order matrix serves as a scaffold for the deposit of collagen type III, which is more rapidly produced, followed by collagen type I. Eventually, the mature scar is composed of primarily collagen type I with smaller amount of collagen type III and virtually no fibronectin (Dobaczewski, M., et al., *Extracellular matrix remodeling in canine and mouse myocardial infarcts*. Cell Tissue Res, 2006. 324(3): p. 475-88). A distinctive feature of the cardiac scar is that the collagen is completely cross-linked, which adds strength to the scar.

A scar does not support large-scale infiltration or engraftment of therapeutic cells, primarily because of the collagen cross-linking and poor circulation. For this reason the scar has largely been abandoned during targeted regenerative medicine treatments. Instead, efforts have focused on the border zone, which contains hibernating cardiomyocytes, better circulation, and a more typical extracellular matrix.

Understanding the spatial and temporal aspects of cardiac healing allows us to create an in vitro environment that more closely resembles the injured myocardium during the various phases of cardiac healing. This in vitro modeling is important to efficiently study therapeutic cell adhesion and targeted treatments to increase engraftment in vivo.

To investigate the adhesion of therapeutic cells to extracellular matrix, we have created three matrix conditions that resemble different phases of cardiac healing. 1) Phase 1 and 2: Peracetic acid was used as a decellularizing agent. This method leaves large quantities of cell debris on the extracellular matrix. 2) Phase 3: Ammonia hydroxide-Triton™ X-100 is used as a decellularizing agent. This method better removes cellular debris, leaving the extracellular matrix proteins exposed. 3) Late phase 3, beginning of phase 4: High density cardiac fibroblast culture was used to resemble the peak of myofibroblasts infiltration. This condition was not decellularized in an attempt to more closely model the scar before a large proportion of the myofibroblasts undergo apoptosis.

Targeted treatments to increase therapeutic cell adhesion in the three conditions were carried out using a novel strategy utilizing a double ended antibody that binds to both CD44 and fibronectin. CD44 is highly expressed on BMSC and fibronectin is the major structural component to the CF 3D-ECM, thus, adhesion should be increased unless the antibody is not able to interact with fibronectin binding sites.

Methods

Generation of CF 3D-ECM.

Figure 7:
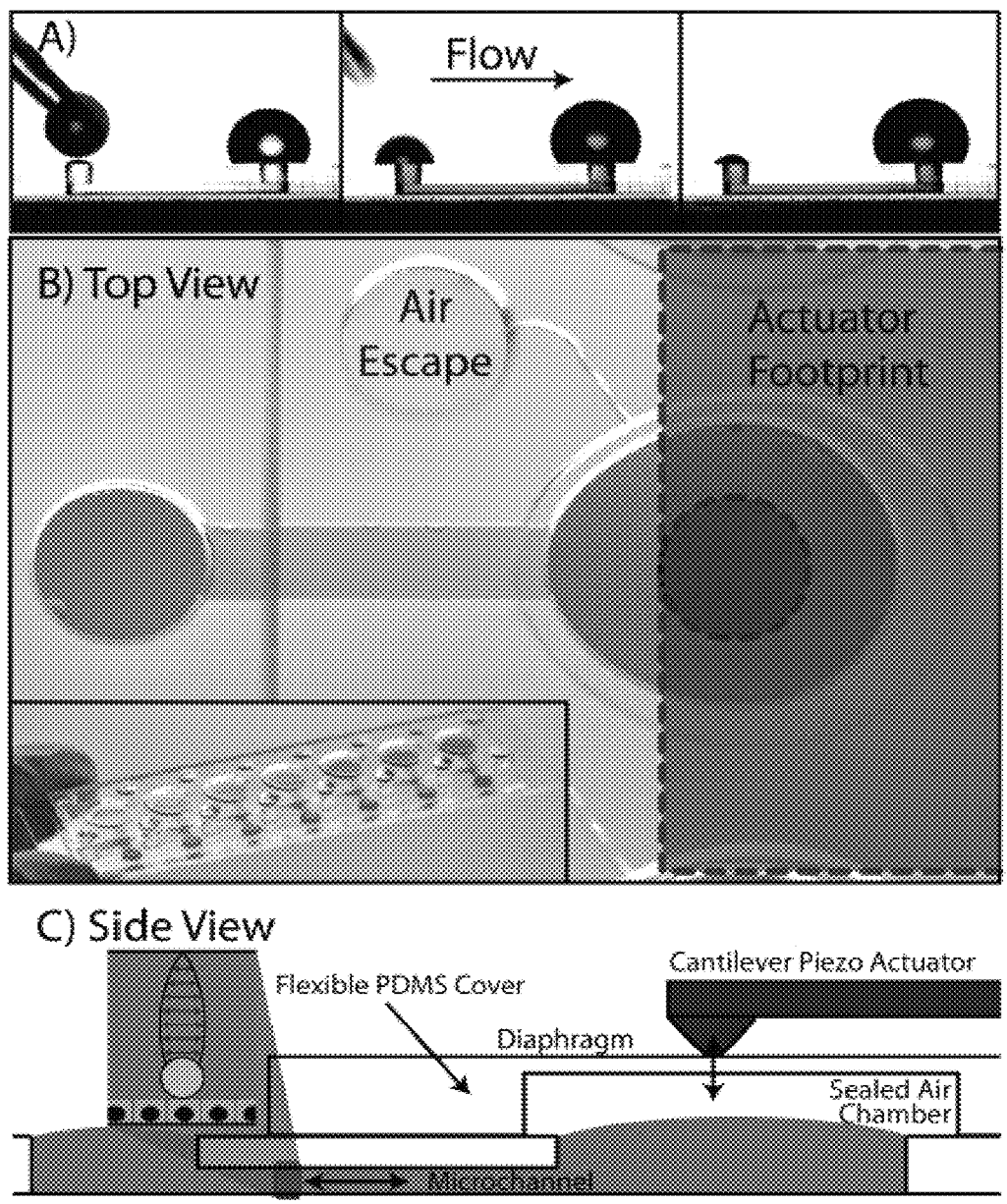
FIG. 7 shows the oscillatory flow device used in the reported experiments. A) Side images of passive pumping via dispensed droplets. B) Top view of microchannel and diaphragm assembly. Inset shows 7×1 array of microchannels on a single microscope slide. C) Side view of setup. Cantilever piezoelectric actuator deflects diaphragm according to applied voltage signals. At low frequency and moderate amplitude, this creates a volume change in the air cavity and displaces fluid in the channel.

Cardiac fibroblasts were isolated as described in Example 1. Cardiac fibroblasts were seeded at a confluent density into the microfluidics devices (FIG. 7), which were provided by the David Beebe lab at the Wisconsin Institute for Medical Research at the University of Wisconsin-Madison. Fibroblasts were cultured in DMEM+10% FBS and 1% penicillin/streptomycin under standard culture conditions (37° C., 5% $CO_2$ and 100% humidity) for 2 hours, then the open ports were scraped free of cells to isolate the CF 3D-ECM in the device channel. Cardiac fibroblasts were further cultured for 10±3 days before decellularization using Method 1 or 2 as described in Example 1. Following decellularization, the CF-3D-ECM was washed repeatedly with PBS followed by 3 washes with serum free DMEM. All experiments were carried out using serum-free DMEM.

Bone Marrow Mesenchymal Stem Cell Isolation.

Bone marrow mesenchymal stem cells (BMSC) were isolated 5-7 days before the experiment using the method in Example 1. The day of the experiment, BMSC were trypsinized, and split into tethered and non-tethered fractions. Non-tethered BMSC were maintained on ice in serum-free DMEM until the experiment.

Antibody Tethering:

CD44 Antibody-Streptavidin Conjugation.

Anti-CD44 antibody from Santa Cruz (10 µg (50 µl)) was linked to streptavidin with the Lightning-Link™ Streptavidin Conjugation Kit (Innova Biosciences) according to manufacturer's directions. Briefly, 5 µl of LL-Modifier reagent was added to 50 µl of anti-CD44 antibody and mixed gently. Anti-CD44 antibody with LL-Modifier was pipetted directly into 10 µg of lyophilized Lightning-Link material and mixed by pipetting. The mixture was incubated overnight at room temperature. 5 µl of LL-quencher reagent was added to 50 µl of streptavidin linked antibody and incubated for 30 minutes at room temperature. Streptavidin conjugated antibody was stored at 4° C. until use.

Bone Marrow Mesenchymal Stem Cell-Antibody Tethering.

Bone marrow mesenchymal stem cells were trypsinized as described above and suspended in 90 µl 2% FBS in PBS. 10 µl of streptavidin-linked CD44 antibody was added and incubated at 4° C. for 30 minutes. Cells were washed with 1 ml 2% FBS in PBS, centrifuged at 1000×g for 5 minutes at 4° C. The antibody labeled cells were then suspended in 90 µl 2% FBS in PBS and 1.5 µg (10 µl) of biotin conjugated anti-rabbit antibody added and incubated at 4° C. for 30 minutes. The cells were washed with 1 ml 2% FBS in PBS, centrifuged at 1000×g for 5 minutes at 4° C. The cells were suspended in 90 µl 2% FBS in PBS and 10 µl rabbit anti-fibronectin antibody added and incubated at 4° C. for 30 minutes. The cells were washed with 1 ml 2% FBS in PBS, centrifuged at 1000×g for 5 minutes at 4° C. Bone marrow mesenchymal stem cells tethered to anti-fibronectin antibody were then suspended in 1 ml serum free DMEM and stored on ice until use in the dynamic adhesion assay.

Oscillatory Dynamic Adhesion Assay.

The microfluidics device developed in the Beebe lab consists of two open ports connected by a microchannel (FIGS. 7B and 7C). This configuration creates passive pumping through the microchannel, allowing for culture of cardiac fibroblasts and the generation of CF 3D-ECM directly in the microchannel (FIG. 7A). To conduct the assay, a diaphragm is used to seal one set of ports, then a cantilever piezoelectric actuator is placed directly over the center of the port in contact with the diaphragm. Voltage applied to the piezoelectric cantilever deflects the diaphragm, displacing the fluid under the diaphragm and resulting in shear-stress in the channel.

A pilot study was performed measuring BMSC adhesion to AH matrix, tissue culture treated plastic (TCP), and TCP+fibronectin under dynamic conditions. BMSC adhered more rapidly to AH matrix than to TCP or TCP+fibronectin (data not shown). Given the large difference in adhesion between TCP, TCP+fibronectin and the AH matrix, we determined that the assay would be appropriate for testing BMSC adhesion to CF 3D-ECM. Dynamic adhesion was measured for AH, PAA, and CF. BMSC adhered to AH at a significantly higher shear stress than PAA ($p<0.003$) or CF ($p<0.0005$). (n=3 animals)

Results

Dynamic BMSC Adhesion to AH-, PAA-CF 3D-ECM, and Cardiac Fibroblasts.

To test cell adhesion, we measured the $\tau_{50}$ (the shear-stress at which 50% of cells are adhered) of BMSC to either AH matrix, PAA matrix, or cardiac fibroblasts (CF). We found that BMSC adhered at a significantly higher shear-stress to the AH matrix than PAA matrix ($p<0.003$) or CFs ($p<0.0005$). BMSC isolated from three animals were tested for each condition, consisting of at least three microchannels per animal per condition (data not shown).

Effects of Tethering Anti-Fibronectin Antibody to BMSC.

The cardiac specific oscillatory dynamic adhesion assay allows for the screening of methods targeted at increasing therapeutic cell adhesion in an in vitro system. We tested the potential for the double ended CD44-fibronectin antibody to affect adhesion to either AH, PAA-matrix, or CF. We found that adhesion of BMSC was not affected by the presence of the double ended CD44-fibronectin antibody (data not shown). BMSC isolated from three animals were tested for each condition, consisting of at least three microchannels per animal per condition.

Discussion

This Example was designed to 1) determine if BMSC adhesion was affected by the three matrix preparations; and 2) use the oscillatory dynamic adhesion assay in conjugation with our 3-dimensional ECM to test a targeted approach to increasing cell adhesion.

Determining if BMSC Adhesion was Affected by the Three Matrix Preparations.

Cardiac healing is a progressive event composed of specific phases. Each phase is accompanied by changes in extracellular matrix structure and composition. We created two different CF 3D-ECMs using PAA or AH and a third non-decellularized condition (cardiac fibroblasts). As described in Example 1, the composition of structural proteins in both AH and PAA matrix is similar to that of the second order matrix formed during granulation tissue formation, but the amount of cellular debris is significantly different between the AH and PAA matrix preparations. Using these two different matrix preparations and cardiac fibroblasts, we were able to show that BMSC adhere under a greater shear stress to a "clean" (AH) matrix compared to the "dirty" (PAA) matrix or CFs.

These findings suggest a window of opportunity for therapeutic cell transfer that may be most amenable to adhesion. We speculate that window may be between 7-14 days post infarction. During this time the infiltrating macrophages have removed most of the dead cells and debris, while myofibroblasts have produced the fibronectin rich second order scar. Injecting therapeutic cells before this time may reduce adhesion due to increased cell debris, while waiting to inject therapeutic cells after the 7-14 day window may result in reduced adhesion because of peaking numbers of myofibroblasts and the formation of a mature scar.

We recognize that the conditions tested do not fully recapitulate a healing myocardium. There are several components not accounted for in this model, such as the presence of immune cells. Additionally, to our knowledge, the shear-stress felt by a cell injected into the myocardium is not known. For that reason, we used a technique called a "sweep". This technique slowly reduces the shear-stress of the assay resulting in the ability to detect adhesion across several orders of magnitude of shear-stress.

Using the Oscillatory Dynamic Adhesion Assay to Test a Targeted Approach to Increasing Cell Adhesion.

We attempted to affect BMSC adhesion to the CF 3D-ECM matrix by tethering BMSC with a double ended CD44-Fibronectin antibody. We were unable to detect a difference in the adhesion rates of the antibody tethered cells compared to the control cells under any condition. There are several possible explanations for this finding. For example, the size of the cell in comparison to the antibodies may have been too great, creating a condition where the antibody was not long enough to reach the fibronectin of the matrix or the antibody interactions not strong enough to increase adhesion. Additionally, the availability of fibronectin for the antibody to interact with could be impacted by spatial organization of the extracellular matrix components of CF 3D-ECM or the amount of cell debris. Finally, we cannot rule out the possibility that the CD44-fibronectin antibody failed to form correctly, as we had no means to assess this. Less likely is the possibility of the antibodies being internalized over the several hours it takes to perform the assay, because we observed no difference in adhesion rates from the beginning to the end of the assay.

Summary.

We were successful in growing CF 3D-ECM in microfluidic channels where BMSC adhesion could be studied under dynamic conditions. We demonstrated that adhesion to CF 3D-ECM was impacted by the method of decellularization. We speculate that the increased presence of cell debris in the "dirty" PAA CF 3D-ECM significantly reduced BMSC adhesion to the matrix. Additionally, the presence of cardiac fibroblasts also significantly reduced the ability of the BMSC to adhere to the underlying matrix. Finally, we failed to demonstrate an increase in cell adhesion with a targeted antibody tethering approach.

Example 3: Cardiac Fibroblast Patches: Successful Adhesion of Epicardial Patch to Epicardium Epicardial patches have emerged as a promising mode of therapeutic cell delivery for cardiac regeneration. One issue with using synthetic or decellularized tissues as patch materials is the inability of the patch to physically adhere to the surface epicardium, often requiring the use of glue or sutures to hold the patch to the heart. If the patch does not maintain firm contact with the surface of the heart, the ability of the cells to transfer is decreased significantly. We demonstrate in this Example that CF 3D-ECM adheres well to the surface of a heart, creating a unique cardiac based platform for therapeutic cell transfer. This work represents collaboration with the laboratory of Professor Brenda Ogle of the Stem cell and Regenerative Medicine Center at the University of Wisconsin-Madison. Nicholas Kouris of Professor Ogle's laboratory provided human mesenchymal stem cells and carried out the CD73 staining and cell counts.

The CF 3D-ECM we have created is cardiac specific, and its protein composition closely mimics a second order matrix formed during granulation tissue formation. The patch is predominantly composed of fibronectin, which is considered an adhesive component of the extracellular matrix. Because of this high fibronectin content, we hypothesized that CF 3D-ECM would adhere well to the surface of a heart, creating a unique cardiac platform for therapeutic cell transfer.

To test this, a mouse myocardial infarction model was used. Epicardial patches composed of either PAA decellularized CF 3D-ECM or a non-decellularized patch were seeded with embryonic stem cell derived human mesenchymal stem cells (hMSC). Patches were placed on the surface of the infarcted myocardium 24 hours after infarction and subjectively evaluated for initial adhesiveness by a blinded impartial third party who has experience placing epicardial patches. Mice were sacrificed 48 hours after patch placement and hearts examined for sign of cardiac patch adhesion. Histology (H&E) was used to detect patches and confocal microscopy used to detect CD73 express in the patch and myocardium.

Methods

Generation of CF 3D-ECM Patches.

The method for CF-3D-ECM patch production is detailed in Example 1. The notable difference is the use of both a PAA decellularized patch ("CF 3D-ECM patch") and a patch that is only lifted off the plate with 2 mM EDTA and not decellularized (cardiac fibroblasts left in patch; "CF patch").

Seeding of Human Mesenchymal Stem Cells (hMSC) onto Patches.

For this experiment two types of patches were used, PAA decellularized and cardiac fibroblast (CF) patches. Decellularized patches were incubated with PAA overnight at 4° C., and then rinsed repeatedly in PBS+1% penicillin/streptomycin. CF patches were removed from the plate just prior to seeding with hMSC. Both PAA CF 3D-ECM and CF patches were rinsed in serum-free DMEM and trimmed to approximately 1 cm squares and seeded with $5 \times 10^5$ hMSC in 5 µl serum-free DMEM for 2 hours prior to placement on the heart.

Myocardial Infarction Model.

Following induction of isoflurane anesthesia (3%), the mouse was intubated with an 18 gauge catheter and placed on a mouse ventilator at 120-130 breaths per minute with a stroke volume of 150 µl and maintained on 2% isoflurane. A left lateral incision through the fourth intercostal space was made to expose the heart. After visualizing the left coronary artery, a 7-0 or 8-0 prolene suture was placed through the myocardium in the anterolateral wall and secured as previously described (Kumar, D., et al., *Distinct mouse coronary anatomy and myocardial infarction consequent to ligation.* Coron Artery Dis, 2005. 16(1): p. 41-4; Singla, D. K., et al., *Transplantation of embryonic stem cells into the infarcted mouse heart: formation of multiple cell types.* J Mol Cell Cardiol, 2006. 40(1): p. 195-200). Coronary artery entrapment was confirmed by observing blanching of the distal circulation (ventricular apex). The lungs were over inflated and the ribs and muscle layers were closed by absorbable sutures. The skin was closed by additional suturing using 6-0 nylon or silk.

Epicardial Patch Placement.

Following induction of isoflurane anesthesia (3%), the mouse was intubated with an 18 gauge catheter and placed on a mouse ventilator at 120-130 breaths per minute with a stroke volume of 150 µl and maintained on 2% isoflurane. A left lateral incision through the fourth intercostal space was made to expose the heart. The heart was visualized and the surface dried with a surgical sponge. The seeded patch was placed directly onto the epicardial surface of the heart with forceps. The patch was then allowed to adhere for 15 minutes before closing the chest. Patch adhesion was subjectively judged with a "sticky factor" by a blinded surgeon who has experience placing epicardial patches. The "sticky factor" ranges from 0-5; 0 being not sticking at all and 5 being completely adhered. After determining the "sticky factor", the lungs were over inflated and the ribs and muscle layers were closed by absorbable sutures. The skin was closed by additional suturing using 6-0 nylon or silk.

Approximately 48 hours after patch placement, mice were sacrificed by inducing deep anesthesia (3% isoflurane) followed by rapid excision of the heart. Hearts were inspected for evidence of patch adhesion then fixed in 3.6% paraformaldehyde for histological analysis.

hMSC Quantification by CD73 Staining.

Slides containing 5 µm heart sections were probed with goat anti-CD73 (Santa Cruz Biotech, Santa Cruz, Calif.) diluted 1:25 in diluting buffer (5% BSA, 0.02% $NaN_3$ in phosphate buffered saline) and incubated overnight at 4° C. Fluorescence was detected with donkey anti-goat Alexa Fluor (AF488, Invitrogen) secondary antibody at 1:200 dilution in preadsorption solution (90% diluting buffer, 5% human serum and 5% mouse serum) for 45 minutes at room temperature. Samples were counter stained and mounted with a DAPCO/DAPI solution (2.5% DABCO, 50% glycerol, and 0.005% DAPI in PBS). Fluorescence emission was detected on a IX71 inverted deconvolution fluorescence microscope (Olympus). Images were acquired with 20× UPlanFluor objective (NA=0.5), coupled with 3.2× magnification (attaining 64× combined magnification). Analysis was performed using Slidebook software (Intelligent Imaging Innovations Denver, Colo.) and with ImageJ (Fiji, open source software). Images were normalized to a secondary antibody control. Positive events were calculated as a percentage CD73 positive divided by total number of nuclei obtained from analysis of at least eight optical fields per sample.

Results

Myocardial Infarction (MI).

We expected to experience some mortality of the mice undergoing experimental MI. To ensure an adequate number of animals for the patch placement experiment, MI was induced in twelve animals. Of the twelve animals, two did not survive the procedure.

Placement of PAA CF 3D-ECM and CF Patches.

Figure 8:
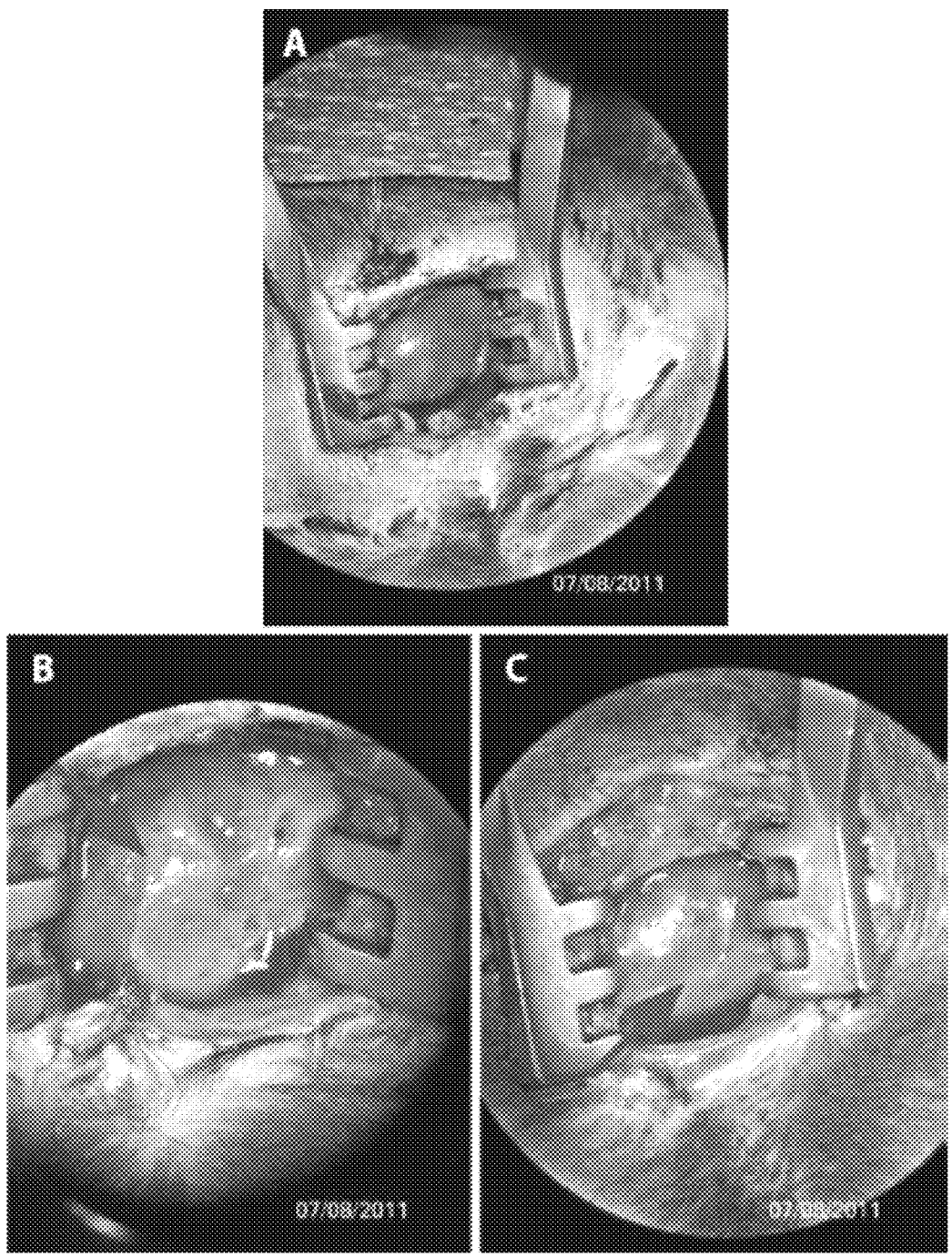
FIG. 8 shows the placement of epicardial patches. A) Representative heart before patch placement. B) A CF 3D-ECM patch placed (arrow). C) A CF patch (arrow), the suture used to occlude the coronary artery is visible under the patch.

Twenty-four hours after induction of MI, the ten surviving mice underwent placement of patches seeded with $5\times10^5$ hMSC; four mice received CF 3D-ECM patches, and four mice received cardiac fibroblast (CF) patches. The remaining two mice served as non-patch controls. Of the mice receiving patches, two did not survive, both from the CF patch group. One mouse did not recover from the patch placement surgery and the second was found dead 48 hours later. Due to this mortality, four mice made up the CF 3D-ECM patch group, two mice made up the CF patch group and two mice were left as non-patch controls. FIG. 8 demonstrates representative examples of CF 3D-ECM and CF patches placed onto the infarcted myocardium.

Assessment of Patch "Sticky Factor."

One drawback to many of the materials investigated as potential epicardial patches is the inability of the patch to adhere or "stick" to the heart. Because CF 3D-ECM is thin, flexible and uniquely cardiac, we hypothesized that it would more readily adhere to the surface of the heart and not require either sutures or fibrin glue to adhere. The assessment of a "sticky factor" (scale=0-5, 0=does not stick at all, 5=completely stuck down) by the impartial, blinded surgeon, was done after the patch had been placed on the surface of the heart for 15 minutes. All four CF 3D-ECM were rated as a sticky factor of 4, all four CF patches were rated as a 3.7. The surgeon noted that the CF 3D-ECM adhered rapidly to the epicardium while CF patches did not, but after 15 minutes the patches appeared to be similarly adhered to the epicardium.

Assessment of CF 3D-ECM and CF Patches 48 Hours after Placement.

Figure 9:
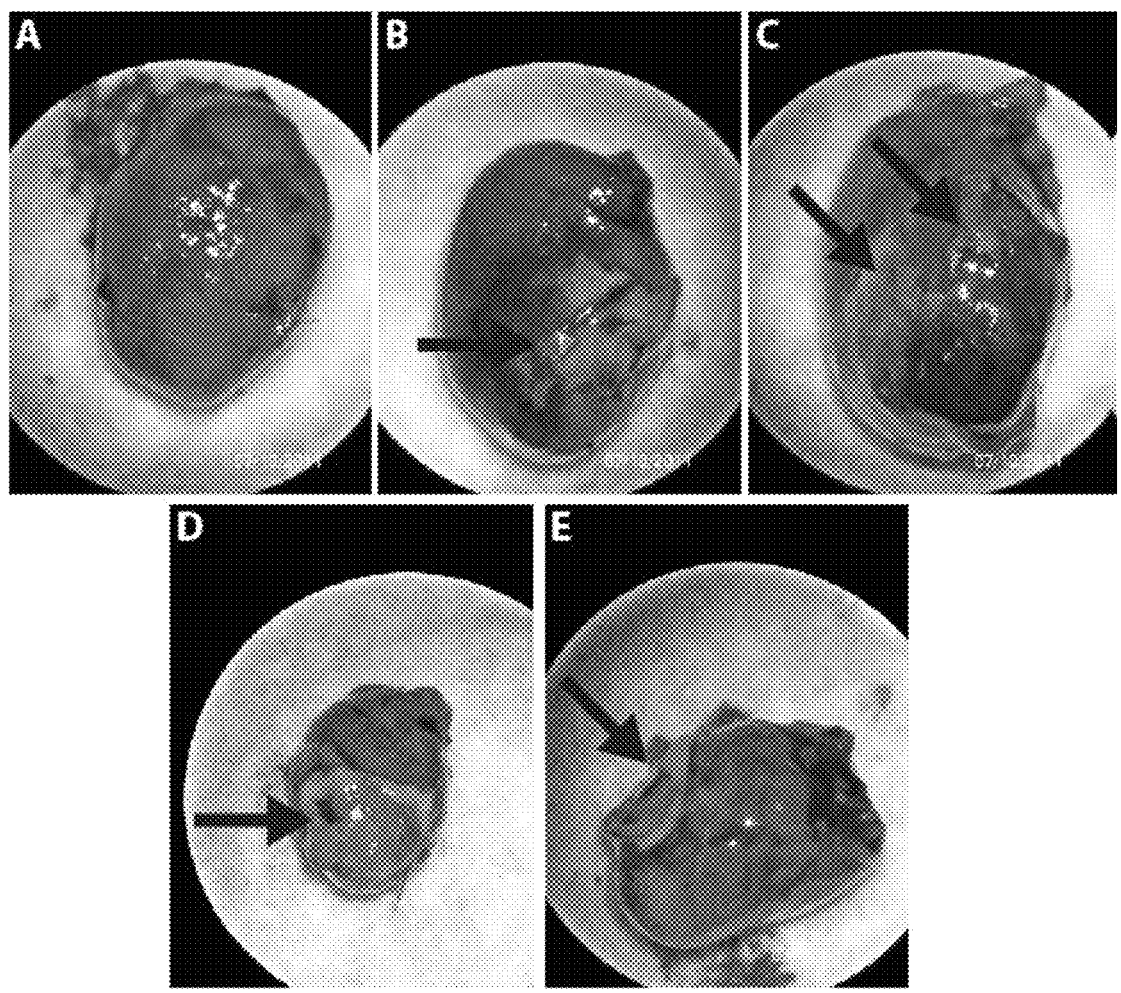
FIG. 9 shows representative examples of control hearts (A), hearts with CF 3D-ECM patches (B,C) and hearts with CF patches (D,E). Arrows indicate patches.

Forty-eight hours after patch placement, mice were sacrificed and hearts examined for evidence of patches. Patches remained at the same site of placement on the epicardial surface of the heart in all animals (FIG. 9). CF patches consistently appeared thicker than CF 3D-ECM patches, as show in FIG. 9.

Histological Examination of Patches.

Figure 10:
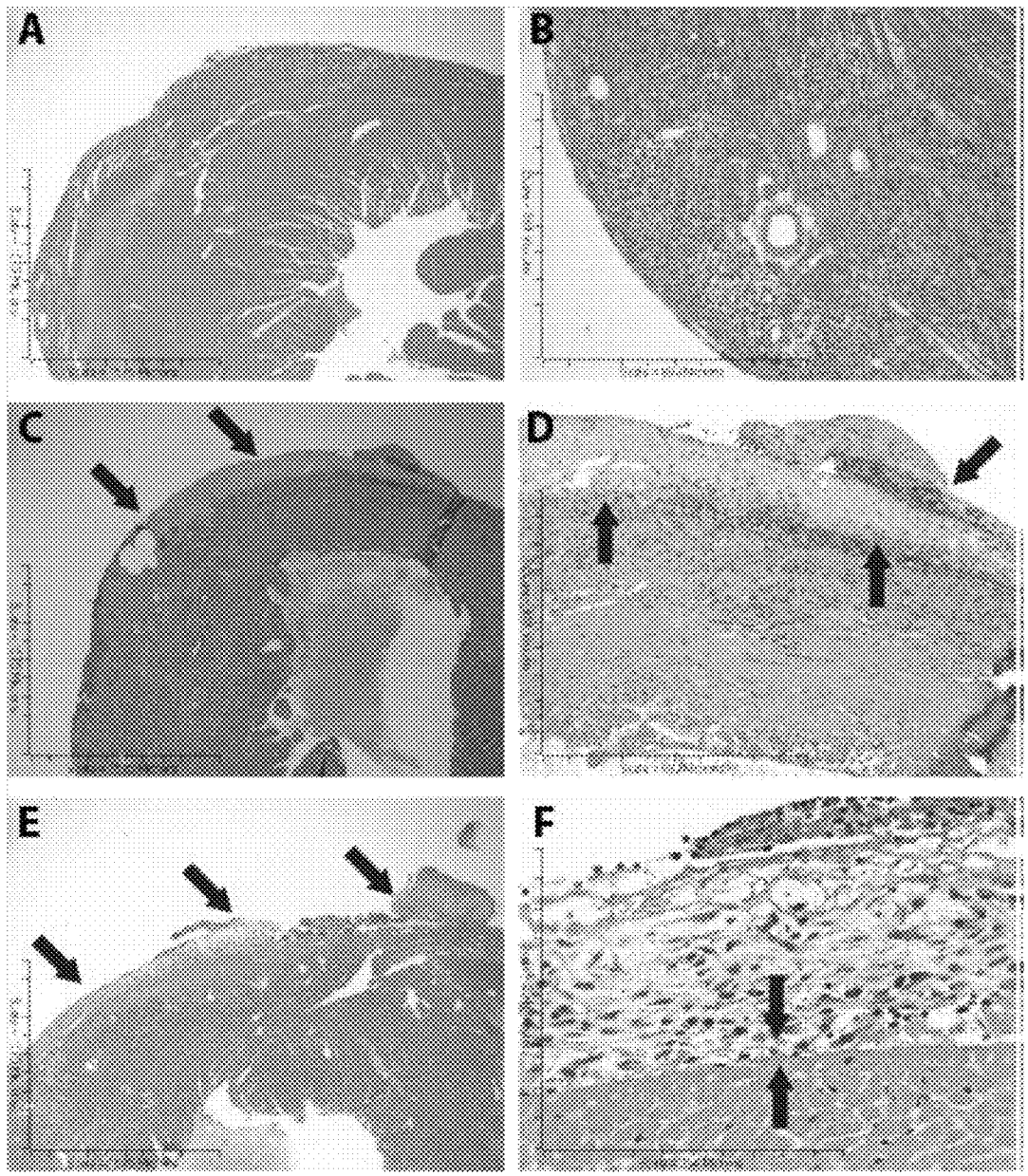
FIG. 10 shows H&E staining of representative hearts (dark spots=nuclei). A) 4× control heart, B) 10× control heart, C) 4× heart with CF 3D-ECM patch, D) 10× heart with CF 3D-ECM patch, E) 4× heart with CF patch (arrows), F) 20× heart with CF patch; arrows depict interface of patch and heart.

Upon removal, hearts were fixed in 3.6% paraformaldehyde, embedded in paraffin, sectioned, and slides stained with hematoxylin and eosin (H&E). Patches were found in all non-control hearts (FIG. 10 A-F).

Figure 11:
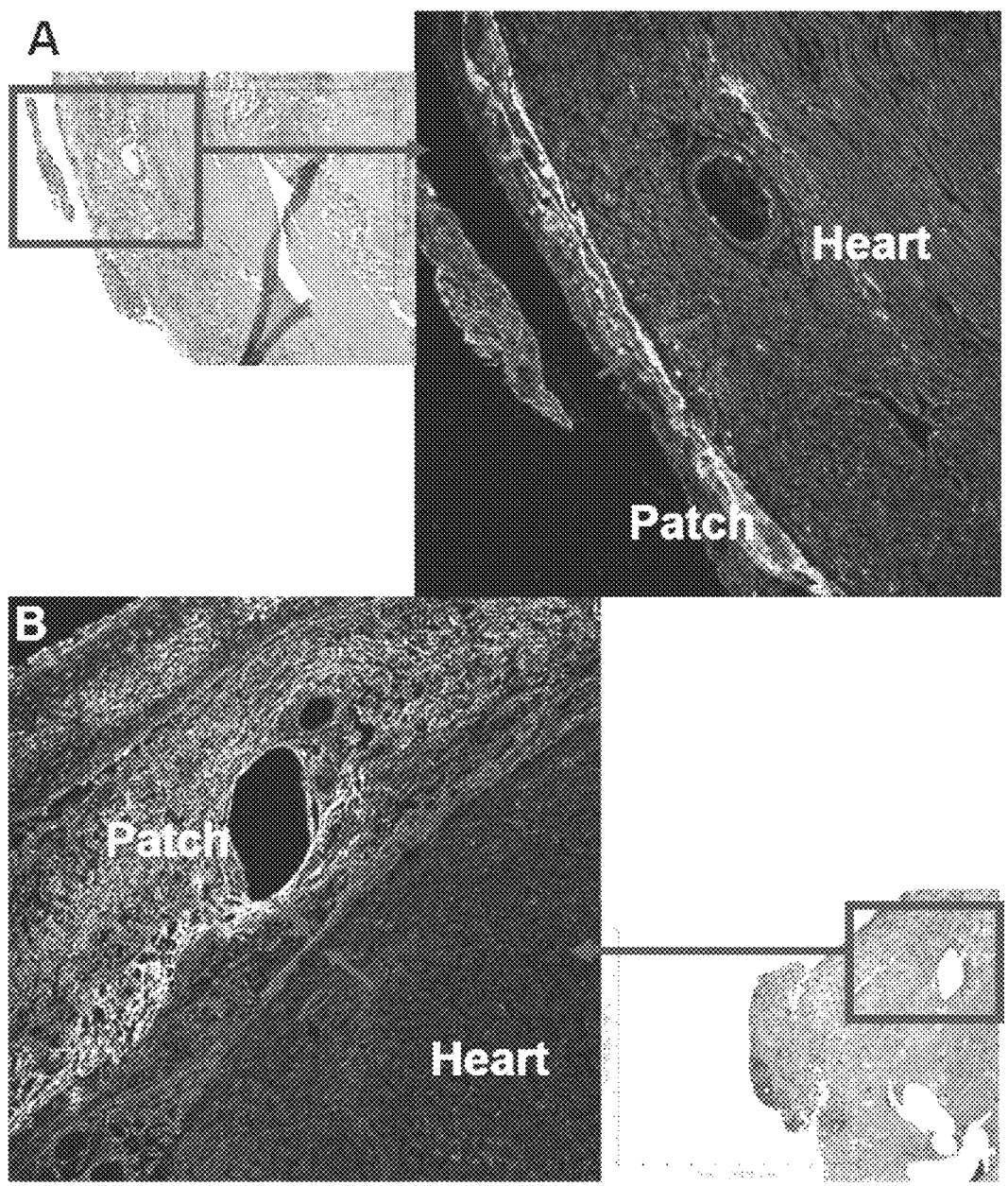
FIG. 11 shows A) H&E staining of CF 3D-ECM patch (left), area in the box is stained for fibronectin and CD146 (right), arrows denote the interface of the patch and heart. B) H&E staining of CF patch (right), area in the box is stained for fibronectin and CD146 (left), arrows denote the interface of the patch and heart.
Figure 12:
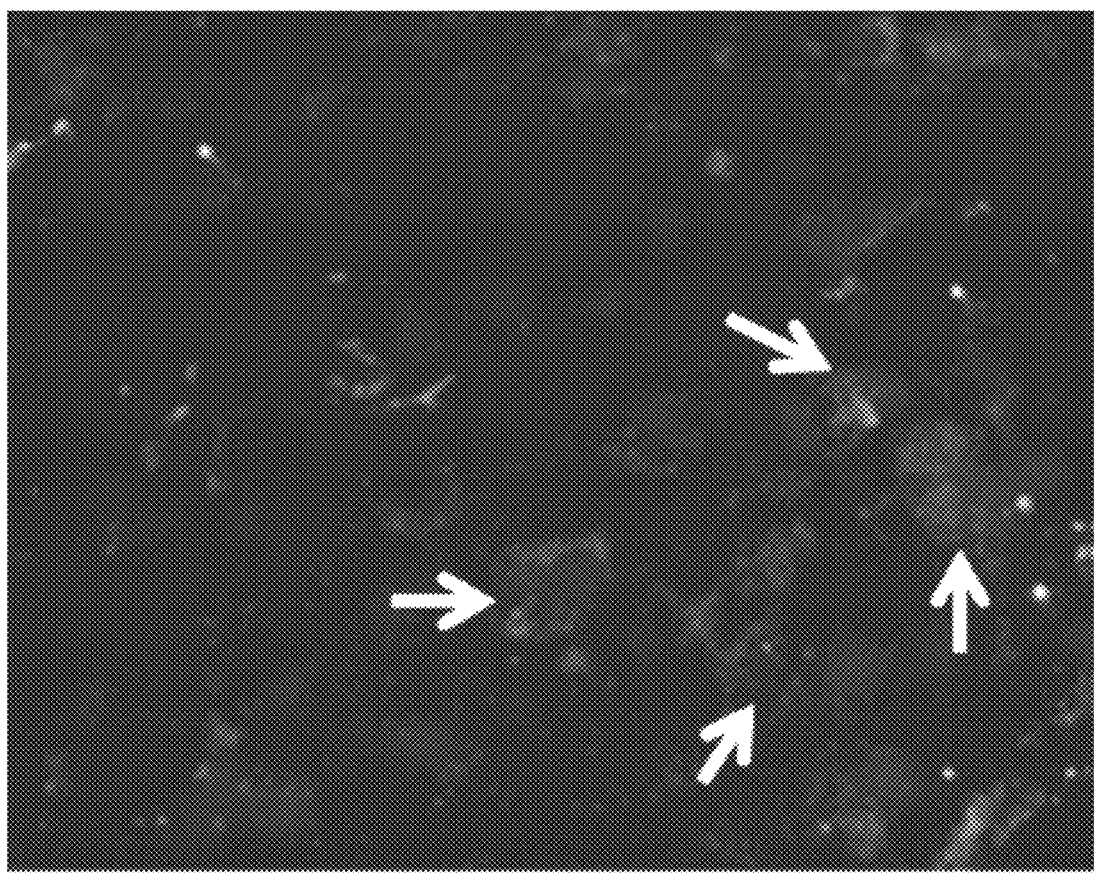
FIG. 12 is a representative example of hMSC CD73 expression in the CF 3D-ECM.

To further evaluate the adhesion of the patch to the epicardial surface of the heart and transfer of hMSCs, immunofluorescence staining was carried out (FIG. 11). To detect the patch, fibronectin was used, while CD146, a MSC marker that is not expressed on fibroblasts, was used to visualize hMSCs. Fibronectin staining was detected, while CD146 was ambiguous. This was due to finding a population of CD146 cells in the control hearts as well. CD146 is also found on epithelial cells as well as some immune cells. We could not differentiate between transplanted hMSCs and host cells.

To quantify the number of hMSC transferred to the infarcted myocardium, we stained for the hMSC marker CD73 (FIG. 22). The patch and underlying myocardium were evaluated for CD73 expression in all eight animals. In the CF 3D-ECM patch group, no CD73 expression was found in two out of the four animals. In the remaining two animals 3.2% and 2.4% of cells in the CF 3D-ECM were positive for CD73. No CD73 positive cells were detected in the myocardium.

In the CF-patch animals 2.9% and 1.4% of the cells in the patch were positive for CD73. No CD73 positive cells were detected in the myocardium.

Discussion

Determining if CF 3D-ECM Patches Will Adhere to the Heart.

Epicardial patch transfer is a promising method of delivering cells to the infarcted myocardium. Of the many synthetic and decellularized tissue patches available, few actually adhere to epicardial surface without the use of sutures or fibrin glue. We accomplished this goal by demonstrating that both CF 3D-ECM patches and CF patches adhere to the epicardial surface and are located at their placement site after 48 hours. Adhesion of the patch to the heart is important for facilitating transfer of cells between the patch and the injured myocardium. As is evident in some of the images, when a piece of patch does not maintain adhesion to the heart, the patch retains a high number of cells (nuclei), presumably the seeded hMSC.

Determining if CF 3D-ECM Patches Will Transfer hMSC to the Infarcted Myocardium.

We were able to find a small percentage of cells in the patch that did express CD73, but no cells were found in the myocardium. There are several possible explanation for this finding. For example, we demonstrated in Example 1 that even a short time in culture on CF 3D-ECM will result in large changes in the gene expression profile of BMSC. Therefore it may be reasonable to expect that the hMSC could have differentiated or lost their CD73 expression. This would not be unexpected since CD73 is stem cell marker and is lost with differentiation. As illustrated in Example 4 below, when using an alternative method of detection (FISH), seeded cells did transfer to the myocardium.

Summary.

In this Example, we demonstrated that CF 3D-ECM patches could be successfully transferred and adhered to the epicardial surface of an infarcted heart. Adhesion of the CF 3D-ECM patch did not result in detectable CD73 expression; however, Example 4 below demonstrates successful transfer of seeded hMSC cells into the myocardium.

Example 4: Cardiac Fibroblast Patches: Successful Transfer of Seeded Cells into Target Myocardium In this Example, we extend our work in the previous examples to (1) further characterize the protein composition of patches, (2) further demonstrate that the patches can be transferred to and maintained on the ventricle, and (3) demonstrate that human mesenchymal stromal cells (hMSCs) can be delivered to healthy and infarcted myocardium using the disclosed ECM patches.

In sum, CFs passage 1-7 from rats were cultured at high density ($\sim 1.6\times10^5/cm^2$) for 10-14 days during which period the cells secreted large amount of extracellular matrix (ECM) to form a manipulable structure that could be removed from the culture dish following incubation with EDTA and peracetic acid. Two-dimensional top down mass spectrometry demonstrated that the patches were primarily composed of fibronectin (81%) with some collagen type I (13%). Additionally, 18 non-structural matricellular proteins were identified. Patches could be seeded with hMSC and the seeded patch successfully attached to the epicardial surface of the murine heart without sutures or added glue. Patches remained intact in vivo for at least 2 days. Even at this early time point, hMSCs were found to migrate more than 500 μm from the epicardium and infiltrated the myocardium in 8 of 11 mice tested. In sum, this example shows that CF-derived ECM can spontaneously attach to and successfully transfer hMSCs to the infracted heart.

Materials and Methods

Animal Care and Use.

Animals were purchased from Harlan Laboratories. All procedures were carried out in accordance with protocols approved by the University of Wisconsin School of Medicine and Public Health Animal Care and Use Committees.

Isolation of Cardiac Fibroblasts.

The technique for isolating cardiac fibroblasts was as performed as described in Example 1. Male Lewis rats (260-400 g) were sacrificed by $CO_2$ asphyxiation, hearts rapidly excised, atria removed and ventricles placed into ice cold PBS with 1% penicillin/streptomycin. Hearts were finely minced then placed into 10 mL digestion media (Dulbecco's Modified Eagle's Medium (DMEM), 73 U/mL collagenase 2, 2 μg/mL pancreatin (4×)) and incubated at 37° C. with agitation for 35 min. The digest mixture was centrifuged at 1000×g for 20 min at 4° C. The resulting cell pellet was suspended in 10 mL of fresh digestion media and incubated at 37° C. with agitation for 30 minutes. The resulting digest was sieved through a 70 μm cell strainer and digest solution diluted with 10 mL of culture media (DMEM, 10% Fetal Bovine Serum (FBS), 1% penicillin/streptomycin). The cell suspension was then centrifuged at 1000×g for 20 min at 4° C. The cell pellet was suspended in 16 mL culture media and plated into two T75 culture flasks (8 mL per flask). The cells were allowed to attach under standard culture conditions (37° C., 5% $CO_2$, 100% humidity) for 2 h, then non-adherent cells removed by washing with PBS and culture media replaced. Primary cardiac fibroblast cultures were typically confluent in 4-7 days.

Generation of CF-ECM.

Cardiac fibroblasts, passage 1-7, were plated at a density of approximately $1.1 \times 10^5$ to $2.2 \times 10^5$ per $cm^2$ in high glucose DMEM+10% FBS and 1% penicillin/streptomycin and cultured at 37° C., 5% $CO_2$ and 100% humidity for 10 to 14 days. Cardiac fibroblasts and secreted extracellular matrix were removed from the culture dish by incubation with 2 mM EDTA solution at 37° C. The resulting cardiac fibroblast cell sheet was then denuded of cells by first rinsing twice with molecular grade water followed by incubation with 0.15% peracetic acid (PAA buffer) for 24-48 hours at 4° C. with constant agitation. The resulting matrix was then rinsed repeatedly with sterile water followed by PBS.

2D Bottom-Up Mass Spectrometry: This procedure was performed as described in Example 1.

In-Solution Trypsin Digestion.

All solutions were prepared fresh just prior to use with HPLC grade water. CF-ECM patches were suspended in 15 μL 8M urea and then 20 μL of 0.2% ProteaseMax™ added. The CF-ECM was then dissolved into solution by vortexting and pipetting. A volume of 58.5 μL of 50 mM $NH_4HCO_3$ was added to a final volume of 93.5 μL. The sample was then reduced by adding 1 μL of 0.5 M DTT and incubating at 56° C. for 20 minutes. 2.7 μL of 0.55 M iodoacetamide was added and incubated for 15 minutes at room temperature in the dark. 1 μL of 1% ProteaseMax™ and 2 μL of 1 μg/μL Trypsin Gold™ were added and incubated overnight at 37° C. The following day 0.5 μL of trifluorocacetic acid was added to the final concentration of 0.5% to stop the reaction.

The sample was then centrifuged at 14,000×g for 10 minutes at 4° C. and the cleared supernatant transferred to a fresh 1.5 mL protease-free tube.

2D Liquid Chromatography Mass Spectrometry.

2 μL of sample was injected onto an Eksigent 2D nanoLC chromatography system and eluted into a Thermo Finnigan LTQ Mass Spectrometer. The sample was retained on an Agilent Zorbax SB300-C8 trap and eluted by reverse phase gradient onto a 0.100 mm×100 mm emitter packed in-house with 5 μm bead 300 Å pore MagicC18 material. Mobile phase solution consisted of a water and 0.1% formic acid aqueous phase and a 0.1% formic acid in 50% acetonitrile: ethanol organic phase. The gradient ran from 1 to 60 min and from 5 to 35% organic with a 95% wash. Eluent was ionized by a positive 3000 V nanoESI and analyzed by a Data Dependent triple play template. The top 5 m/z were selected by intensity, charge state was analyzed by zoom scan, and MS/MS were performed with wideband activation, dynamic exclusion of 1 for 60 s with a list of 300 m/z and a width of +/−1.5/0.5 m/z, collision energy of 35%, and noise level of 3000NL. Sequest searches were performed via Bioworks 3.0 using a downloaded Swissprot database for Rat (October 2010) and its reversed sequences. Search parameters included trypsin digestion, 1 missed cleavage, amino acid length of 6 to 100 with tolerance of 1.4 da, dynamic modifications of methionine methylation (+14 da), and cysteine carboxyamidomethylation (+57 da). Results were filtered to less than 5% false discovery rate, defined by number of proteins identified with reversed sequences divided by the total number proteins identified minus reversed number, and multiplied by 100.

Confocal Microscopy.

This procedure was performed as described in Example 1. CF-ECM patches were fixed in fresh 3.6% paraformaldehyde, embedded in paraffin and sectioned in 5 μm sections and mounted on slides. Slides were de-paraffinized followed by rehydration. Slides were incubated with 0.1% trypsin and a sodium citrate heat retrieval was performed by incubation in 10 mM sodium citrate, 0.05% Tween-20 buffer pH 6 for 60 minutes in an Oster® rice steamer (95-100° C.). Slides were blocked with 1% bovine serum albumin in PBST for 1 hour at room temperature then incubated with primary antibodies (all antibodies purchased from Santa Cruz Biotechnology) at a dilution of 1:50 and incubated at 37° C. for 1 hour. Slides were then washed in PBST and incubated in secondary antibodies at 1:1000 dilution in 1% bovine serum albumin in PBST (all secondary antibodies purchased from Invitrogen) for 1 hour at room temperature in the dark. Slides were washed in PBST and counter stained with 1 μg/mL DAPI for then cover slips mounted with aqueous mounting media and the edges sealed with quick dry, clear nail polish. Slides were imaged at the W. M Keck Laboratory for Biological Imaging with a Nikon AIR scanning confocal microscope.

Scanning Electron Microscopy.

Sample preparation and imaging were carried out by the Biological and Biomaterials Preparation, Imaging, and Characterization Facility at University of Wisconsin Madison. Briefly, ECM samples were diced with a double sided razor blade to approximately 3 $mm^2$ then fixed in 1% paraformaldehyde, 2% glutaraldehyde in 0.1M sodium cacodylate buffer overnight at 4° C. Samples were washed twice in molecular grade water then secondary fixation carried out by incubated with 1% osmium tetroxide (in water) for 30 minutes. Samples were washed twice in molecular grade water then dehydrated with a series of 10 minute ethanol incubations (30, 50, 70, 75, 80, 90, 95, and 100%) and sieve dried. Samples were then critical point dried in a Tousimis Samdri 780 four times and ion beam sputter coated with 2.5 nm of platinum. Finally, the prepared samples were imaged on a Hitachi 5900 High Resolution Field Emission Microscope.

Murine Myocardial Infarction.

Myocardial infarction was carried out as previously described (Kumar, D., et al., *Distinct mouse coronary anatomy and myocardial infarction consequent to ligation.* Coron Artery Dis, 2005. 16(1): p. 41-4). Following induction of isoflurane anesthesia (3%), the mouse was intubated with an 18 gauge catheter and placed on a mouse ventilator at 120-130 breaths per minute with a stroke volume of 150 µl and maintained on 2% isoflurane. A left lateral incision through the fourth intercostal space was made to expose the heart. After visualizing the left coronary artery, a 7-0 or 8-0 prolene suture was placed through the myocardium in the anterolateral wall and secured as previously described (Singla, D. K., et al., *Transplantation of embryonic stem cells into the infarcted mouse heart: formation of multiple cell types.* J Mol Cell Cardiol, 2006. 40(1): p. 195-200). Coronary artery entrapment was confirmed by observing blanching of the distal circulation (ventricular apex). The lungs were over inflated and the ribs and muscle layers were closed by absorbable sutures. The skin was closed by additional suturing using 6-0 nylon or silk. A total of 16 mice (5 sham, 11 MI) underwent thoracotomy. Of these, 11 survived the required 48 hours for patch placement and study (3 shams, 8 MI).

Human mesenchymal Stromal Cells, Patch Seeding and Placement.

H9 human embryonic stem cell derived mesenchymal stromal cells (hMSC) passage 7 were received as a gift from Dr. Jaehyup Kim and Dr. Peiman Hematti of University of Wisconsin-Madison and used as the therapeutic cellular reagent. Twenty four hours post infarction; patches were seeded with hMSCs for 2 hours prior to transfer to the epicardial surface of the MI area. The chest was left open for 15 min to allow the patch to seat down prior to closing. Forty-eight hours after the patch was transferred, mice were sacrificed and hearts examined.

Fluorescence In Situ Hybridization (FISH).

FISH was carried out according to manufacturer's instructions using the Tissue Digestion Kit 1 (Kreatech KBI-60007). Briefly, slides were de-paraffinized by baking at 56° C. for 4 hours, followed by xylene incubation. Slides were rehydrated followed by incubation in 96-98° C. Pretreatment Solution A, then rinsed in water and digested with 200 µl Pepsin Solution for 50 minutes at room temperature. Digestion was stopped by rinsing in water and incubating in 2×SSC buffer at room temp. Slides were dehydrated, then 10 µL All Human Centromere Probe (Kreatech KI-20000R) applied to the sample, sealed with a cover slip and incubated at 80° C. for 5 minutes. Slides were then incubated overnight at 37° C. Slides were washed in Wash buffer II and the cover slip removed then washed in Wash buffer I at 72° C. Finally, the slides were washed in Wash buffer II, dehydrated and allowed to air dry. Slides were counter stained with DAPI and a cover slip mounted.

Results.

Generation of CF-ECM Patch.

We found that cardiac fibroblasts cultured at high densities for 10-14 days could be removed as a cell sheet by incubation with 2 mM EDTA. Duration of culture was dependent primarily on seeding density. The resulting cardiac fibroblast "sheet" could subsequently be decellularized to create a cardiac specific extracellular matrix patch, as shown in FIG. 2.

Characterization of CF-ECM Patch.

Figure 13:
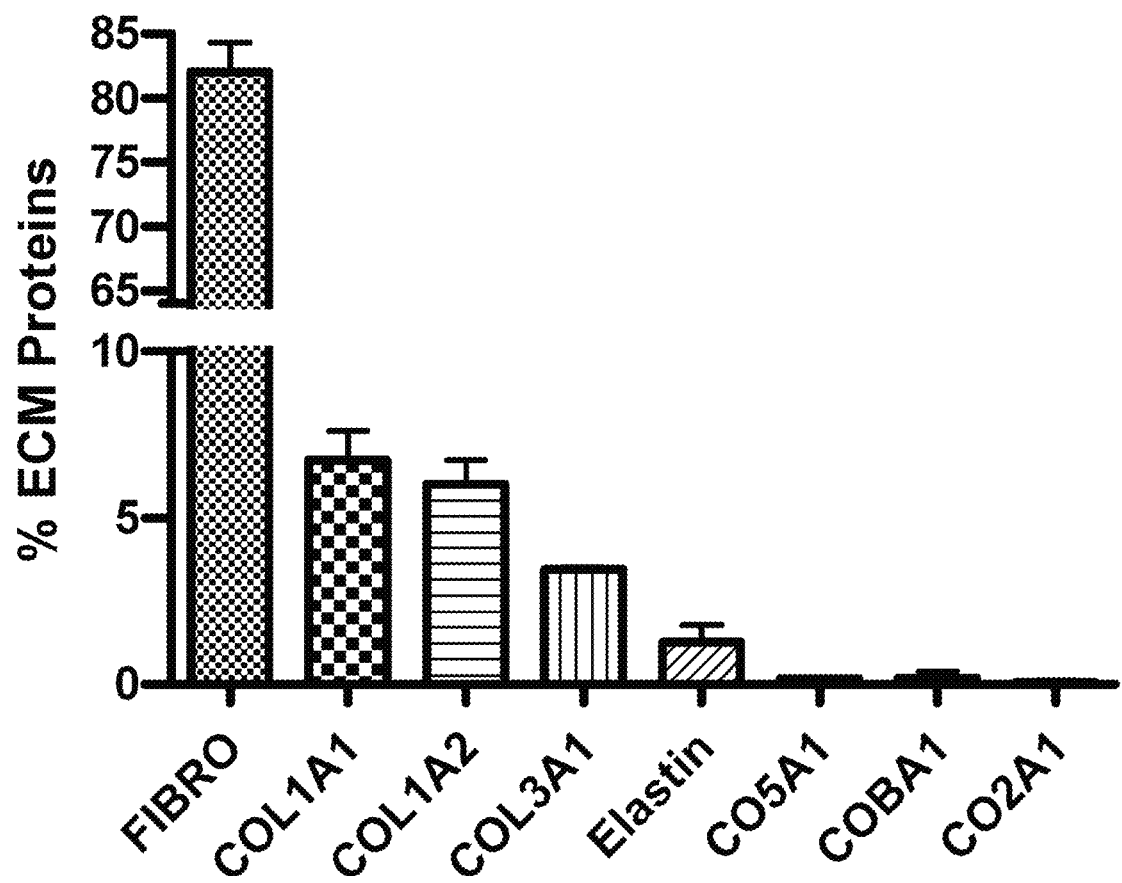
FIG. 13 is a bar graph showing the protein composition of the CF-ECM patch. Note the high fibronectin content.

To characterize the protein composition of the CF-ECM patch, two-dimensional mass spectrometry was performed (n=4). Normalized spectral abundance factor (NSAF) was used to quantify the abundance of structural extracellular matrix proteins (FIG. 13). Fibronectin (82.1+/−2.2%) was found to be the primary component of the matrix with collagen type I (6.7+11 0.9% collagen 1A1 and 6.0+/−0.7% collagen 1A2) and collagen type III (3.4+/−0.08%) accounting for a lesser proportion of the matrix. Additionally, small amounts of elastin (1.3+/−0.5%), collagen types II (0.1+/−0.007%), V (0.2+/−0.06%) and XI (0.2+/−0.2%) were detected. Additionally, 18 matricellular proteins were identified (Table 2). Due to the low abundance of matricellular proteins, meaningful quantification was not possible.

TABLE 2

| Matricellular proteins Detected in Cardiac ECM Matricellular Proteins |
| --- |
| Transforming growth factor beta 3 |
| Latent transforming growth factor beta 1 |
| Latent transforming growth factor beta 2 |
| Connective tissue growth factor |
| Galectin 1 |
| Galectin 3 |
| Galectin 3 binding protein |
| Matrix metaloprotease 14 |
| Matrix Gla Protein |
| Granulings |
| SPARC |
| Versican Core Protein |
| Nidogen 1 |
| VonWillebrand factor A5 A |
| Prothrombin |
| Biglycan |
| Glia derived nexin |
| Sulfated glycoprotein 1 |

Figure 14:
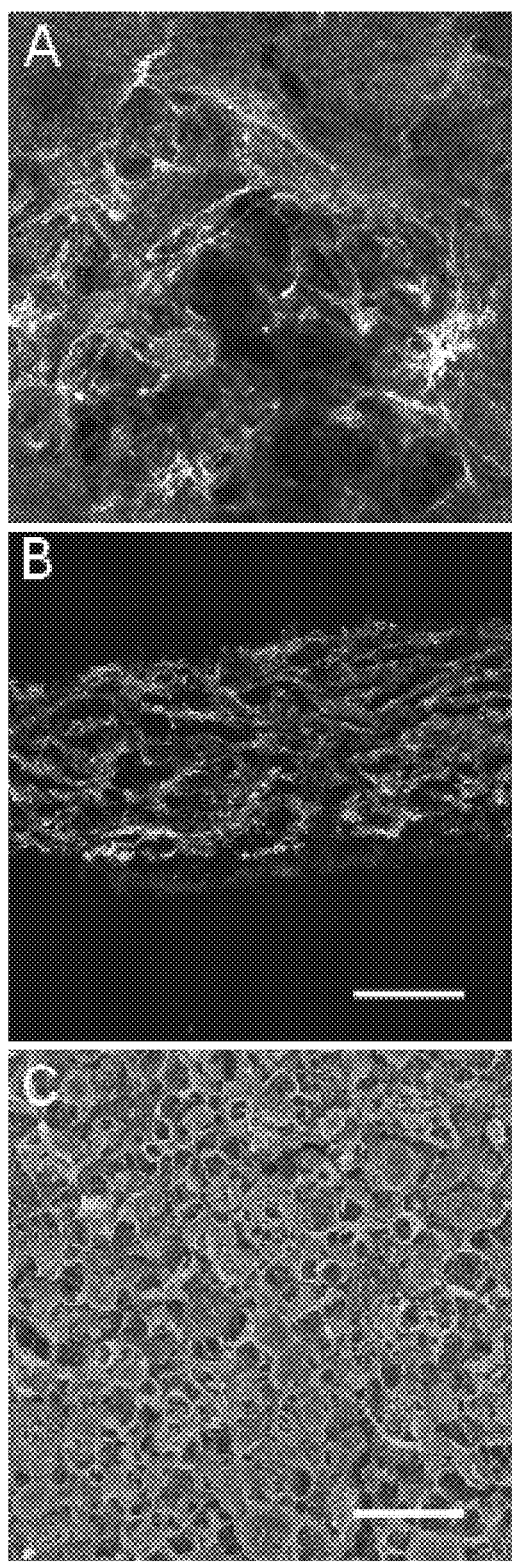
FIG. 14 shows photographs of CF-ECM patch. A) Shows surface staining for CF-ECM patch. B) Shows cross section of CF-ECM patch, stained for fibronectin, collagen type I, and DAPI (colors not shown) (scale bar=50 μm). Note the thickness of approximately 150 μm. C) Shows scanning electron micrograph of CF-ECM surface (scale bar=40 μm).

To evaluate the architecture of the extracellular matrix patch, immunofluorescence microscopy for collagen type I and fibronectin were carried out. The surface of the decellularized patches were visualized by fixing and staining (FIG. 14A) while the internal architecture was visualized by embedding patches in paraffin and cutting into 5 µm sections (FIG. 14B). Both surface and internal staining corroborated the two-dimensional mass spectrometry findings of a matrix rich in fibronectin as well as smaller amounts of collagen type I, which primarily localized to the surface of the matrix. High resolution imaging of the surface of the CF-ECM patch using scanning electron microscopy revealed a honeycomb like architecture with some cell membranes and debris present (FIG. 14C).

Attachment of CF-ECM Patch to Epicardium and Transfer of hMSCs into the Murine Myocardium.

To determine if the cardiac extracellular matrix patch could attach to the epicardial surface without the use of suture or glue, mouse myocardial infarction and sham models were used. A total of 16 mice (5 sham, 11 MI) underwent thoracotomy. Twenty four hours post infarction, patches seeded with hMSCs were transferred to the epicardial surface of the MI area (FIG. 15A). The chest was left open for 15 minutes to allow the patch to seat down prior to closing. Eleven mice survived at least 48 hours at which point the mice were sacrificed and hearts examined (FIG. 15B). Epicardial patches were adhered to the surface of the heart in 11 of 11 mice. In five of eleven mice, minor adhesion of the patch to the chest wall or lungs, mostly at the edges of the patch, was observed. Epicardial patch attachment to the heart was confirmed by hematoxylin/eosin (FIG. 15C) and immunofluorescence staining for fibronectin (FIG. 15D).

Figure 15:
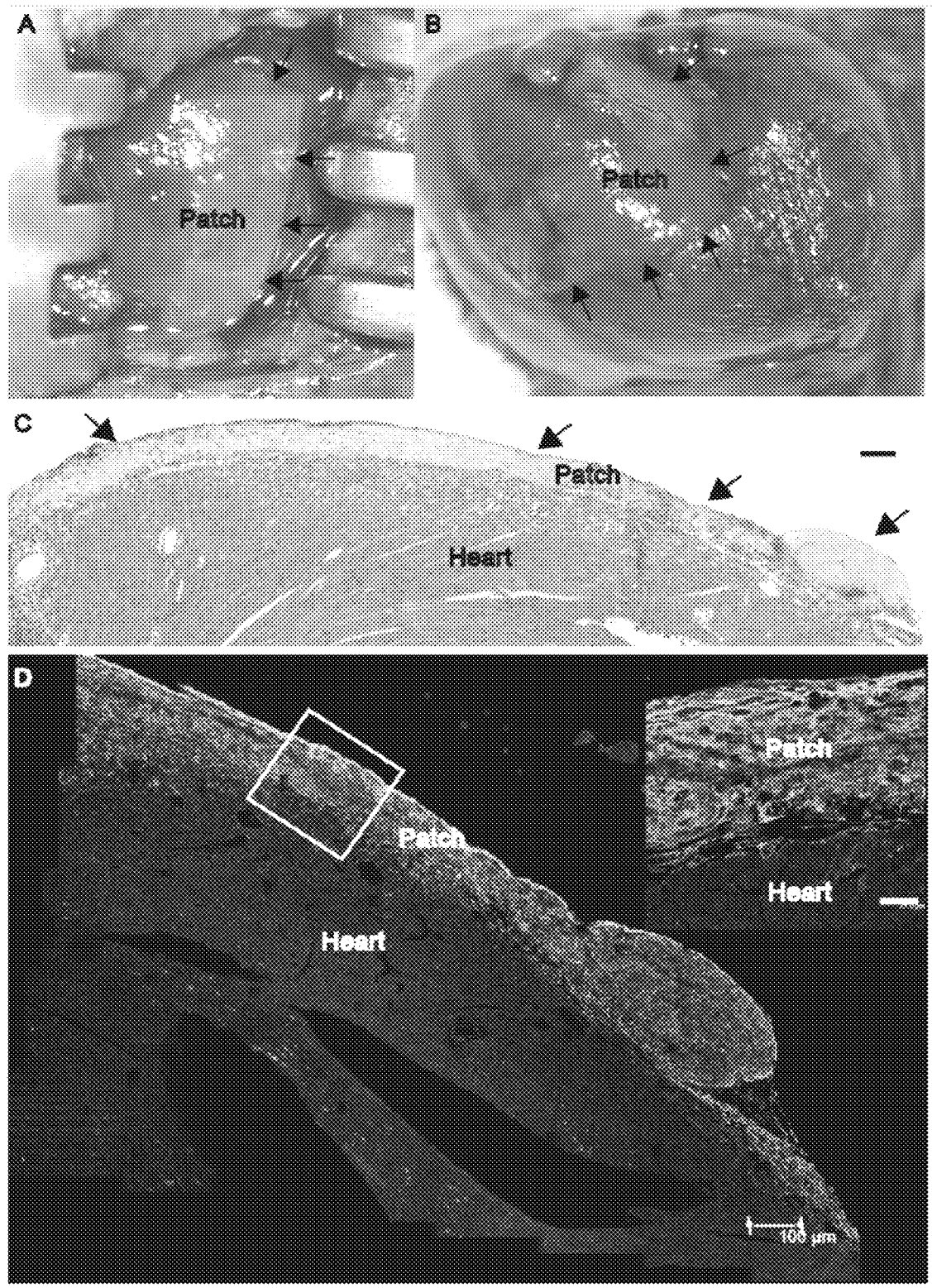
FIG. 15 shows photographs of CF-ECM patch. A) Shows CF-ECM at time of placement on the mouse heart (0 h), arrows denote the edge of the patch. B) Shows attached patch after 48 h on the beating mouse heart, arrows denote the edge of the patch. C) Shows hematoxylin and eosin stain of a cross-section of the epicardial surface, arrows denote the patch. Note the absence of gaps between the patch and epicardial surface (scale bar=100 μm). D) Shows immunofluorescence micrograph of an attached patch after 48 hours on the beating mouse heart (scale bar=100 μm). Inset image denotes the tight attachment between CF-ECM patch and the epicardial surface. Stained for Fibronectin and DAPI (colors not shown) (scale bar=25 μm).
Figure 16:
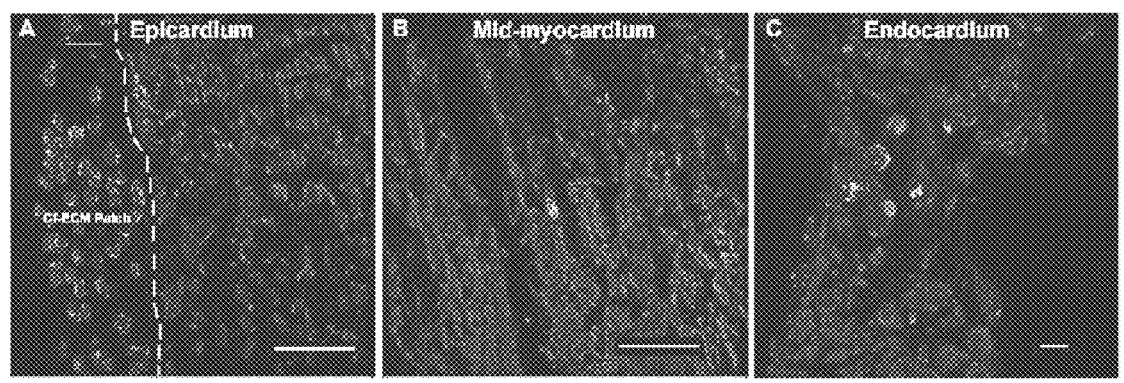
FIG. 16 shows photographs of FISH staining for human centromeres (bright spots). Nuclei indicates the presence of human cells within the mouse heart. Note that cardiomyocytes are highly autofluorescent helping to distinguish hMSCs from myocytes. A) The epicardial surface with attached patch, note the presence of hMSCs in the CF-ECM patch. The dashed line indicates the interface between the CF-ECM patch and the epicardium (scale bar=50 μm). B) Mid-myocardium with human nuclei (scale bar=50 μm). C) Endocardial surface with human nuclei present (scale bar=10 μm).

Evaluation of hMSCs transfer to the infarcted or sham myocardium was carried out using FISH (FIG. 15). As detailed in Table 2, nuclei staining positive for human centromeres were detected in the adhered extracellular matrix patch in 11 of 11 animals (FIG. 16A). Infiltration of hMSCs into the myocardium was detected in 8 out of 11 animals with cells primarily residing within 500 µm of the epicardial surface (FIG. 16B). In 2 out of 11 samples, hMSCs were detected greater than 500 µm from the epicardial surface. In one sample, hMSCs were localized to the endocardial surface of the heart (FIG. 16C).

Discussion

The initial goal of our study was to determine if cell culture and decellularization techniques could be employed to generate an ECM patch from cardiac fibroblasts that harbored structural, mechanical and biochemical properties necessary for a potential cell-transfer platform. Once this goal was accomplished we proceeded to define the biochemical and histological properties of the patch. Finally, we determined two key physiological features of the patches in vivo: 1) attachment to epicardium, and 2) the ability to bind and release hMSCs thereby acting as a platform for cell transfer.

The CF-ECM patch presented in this example has several notable features which merit discussion; specifically, its physical characteristics and its biochemical composition. We found that physical characteristics of the patch such as size, shape and thickness could be manipulated by varying the size (up to a T75 culture flask) and/or shape of the culture vessel, as well as plating density and length of time in culture (data not shown). These features are especially important should this technology be used in larger animal models and human applications. It is also important to note that the CF-ECM patch is robust enough to allow for physical manipulation during the transfer process. Additionally, the decellularization process developed for the production of CF-ECM patches did not employ chemical cross-linking. This may have important implication in the immune response and healing process. For example, recent studies show that ECM patches that are not chemically crosslinked promote the infiltration and activation of anti-inflammatory macrophages (M2) (see, e.g., Freytes, D. O., L. Santambrogio, and G. Vunjak-Novakovic, *Optimizing dynamic interactions between a cardiac patch and inflammatory host cells*. Cells Tissues Organs, 2012. 195(1-2): p. 171-82). These cells have been shown to be associated with immune-regulatory, remodeling, matrix deposition, and graft acceptance.

To better understand the biochemical nature of the CF-ECM, we used two-dimensional mass spectrometry. To our knowledge, this is the first rigorous characterization of a fibroblast derived matrix. To date, others studying various fibroblast derived ECM have used antibody based microscopy techniques instead of a discovery tool such as mass spectrometry to investigate the composition of the ECM. The CF-ECM was found to be predominately fibronectin with lesser amounts of collagens and elastin.

Interestingly, the proportions of ECM proteins found in CF-ECM is similar, but not identical, to that of a healing myocardium following infarction; bearing similarity to the "second order" (fibronectin) scar, which occurs approximately 14 days post infarction (Dobaczewski, M., et al., *Extracellular matrix remodeling in canine and mouse myocardial infarcts*. Cell Tissue Res, 2006. 324(3): p. 475-88). These findings may indicate that CF-ECM in vitro may recapitulates aspects of in vivo cardiac healing and thus be a useful new tool for studying the cardiac healing process.

Finally, in regards to biochemical properties of CF-ECM, it is important to note that we were able to reproducibly detect 18 matricellular proteins using two-dimensional mass spectrometry, as shown in Table 2. These bioactive molecules include growth factors and cytokines are involved in important cellular properties such as adhesion, de-adhesion, proliferation, and differentiation.

Implantable biomaterials in the form of epicardial patches may significantly increase cellular retention by creating a platform from which therapeutic cells can infiltrate the damaged myocardium. Patch attachment to the epicardial surface is an integral component of the cell transfer strategy. Inherent adhesiveness of the patch is a property not currently found in most patches, thus the use of suture or glue to affix the patch to the surface of the heart is common. This strategy has the risk of increasing myocardial damage by restricting small vessels, while tissue glues may not only cause irritation to the surface of the heart but may also inhibit cell migration by acting as a barrier to both cells and chemokine signals. We found the CF-ECM patches to be adherent in both sham and MI models after an estimated 1.5 to 2 million heart beats.

Although we did not test the specific nature of the attachment, we speculate that fibronectin plays a key role due to its expression of multiple binding sites for collagen, fibrin/fibronectin, vitronectin, heparin, and cells (through a variety of cell surface integrins). The high fibronectin content of the CF-ECM patch may have additional benefits in the healing myocardium as it has been shown to induce cell proliferation, adhesion, survival, and angiogenesis (see, e.g., Berger, S., et al., *Short-term fibronectin treatment induces endothelial-like and angiogenic properties in monocyte-derived immature dendritic cells: Involvement of intracellular VEGF and MAPK regulation*. Eur J Cell Biol, 2012).

It should be recognized that the composition of the CF-ECM depends on culture conditions. This raises the possibility that the composition of the CF-ECM could be experimentally controlled for different clinical application. For example, the composition of a patch intended for treatment or preventing of cardiac dilation or an aneurysm may require a stronger patch perhaps containing more collagen type I.

In summary, we found that the CF-ECM described in this example not only adhered to the epicardial surface of the heart, but allowed hMSCs to transfer into the myocardium in 9 out of 11 animals tested. This indicates that the hMSCs could reversibly bind to the CF-ECM. Transfer of cells was not limited to the epicardial surface immediately under that patch, but instead hMSCs consistently migrated within the first 500 µm of the myocardium. This cellular migration occurred during a relatively brief (48 hour) period and does not appear to be dependent on an "injury signal" since sham as well as MI hearts demonstrated migration. In both an MI and sham animal, hMSCs had migrated to near the endocardial surface.

Example 5: Increased Plating Density to Make Cardiac Fibroblast 3-Dimensional Extracellular Matrix In this Example, we report the results of increasing the plating density of the expanded cardiac fibroblast culture that secretes the disclosed 3-dimensional cardiac extracellular matrix. We performed the procedures outlined in the previous examples, except that we used higher plating densities than reported in the previous examples. We investigated plating densities of up to 500,000 cells per cm². Our results demonstrate that these higher plating densities worked just as well as the previously reported plating densities. However, at plating densities below 100,000 cells per cm², the 3-dimensional cardiac extracellular matrix patches do not reliably form.

All references listed in this application are incorporated by reference for all purposes. While specific embodiments and examples of the disclosed subject matter have been discussed herein, these examples are illustrative and not restrictive. Many variations will become apparent to those skilled in the art upon review of this specification and the claims below.

We claim:

1. A method for preparing a 3-dimensional cardiac extracellular matrix, comprising:
   (a) isolating cardiac fibroblasts from cardiac tissue;
   (b) expanding the cardiac fibroblasts in culture for 1-7 passages;
   (c) plating the expanded cardiac fibroblasts into a culture having a cell density of 100,000 to 500,000 cells per cm², wherein the cardiac fibroblasts secrete a 3-dimensional cardiac extracellular matrix having a thickness of 20-500 μm that is attached to the surface on which the expanded cardiac fibroblasts are plated; and
   (d) contacting the cardiac extracellular matrix with a decellularizing agent, whereby the 3-dimensional cardiac extracellular matrix is decellularized to produce a decellularized 3-dimensional cardiac extracellular matrix comprising structural proteins fibronectin, collagen type I, collagen Type III, and elastin, wherein from 60% to 90% of the structural protein molecules present in the 3-dimensional cardiac extracellular matrix are fibronectin.

2. The method of claim 1, wherein the cardiac extracellular matrix has a thickness of 30-200 μm.

3. The method of claim 2, wherein the cardiac extracellular matrix has a thickness of 50-150 μm.

4. The method of claim 1, further comprising the steps of contacting the secreted cardiac extracellular matrix with ethylenediaminetetraaceticacid (EDTA), whereby the cardiac extracellular matrix becomes detached from the surface, forming a free floating bioscaffold.

5. The method of claim 1, wherein the decellularizing agent comprises peracetic acid or a mixture comprising ammonium hydroxide and octylphenol ethylene oxide (Triton™ X-100).

6. The method of claim 1, further comprising the step of seeding the cardiac extracellular matrix with one or more cells that are therapeutic for cardiac disease or injury.

7. The method of claim 6, wherein the one or more cells that are therapeutic for cardiac disease or injury are selected from the group consisting of skeletal myoblasts, embryonic stem cells (ES), induced pluripotent stem cells (iPS), multipotent adult germline stem cells (maGCSs), bone marrow mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesochymal stem cells, and human mesenchymal stem cells (derived from iPS or ES cells), or combinations thereof.

8. The method of claim 1, wherein the cardiac extracellular matrix is essentially devoid of intact cardiac fibroblast cells.

* * * * *

UNITED STATES PATENT AND TRADEMARK OFFICE
CERTIFICATE OF CORRECTION

PATENT NO. : 9,744,265 B2  
APPLICATION NO. : 14/330486  
DATED : August 29, 2017  
INVENTOR(S) : Eric G. Schmuck and Kurt W. Saupe Page 1 of 1

It is certified that error appears in the above-identified patent and that said Letters Patent is hereby corrected as shown below:

In the Specification

Column 2, Line 38 - "of at least 20" should be --of at least 20 µm.--

Column 13, Line 60 - "300 of" should be --300 µl of--

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*